(12) United States Patent
Messerly et al.

(10) Patent No.: US 11,925,378 B2
(45) Date of Patent: Mar. 12, 2024

(54) ULTRASONIC TRANSDUCER FOR SURGICAL INSTRUMENT

(71) Applicant: Cilag GmbH International, Zug (CH)

(72) Inventors: Jeffrey D. Messerly, Cincinnati, OH (US); Brian D. Black, Loveland, OH (US); William A. Olson, Lebanon, OH (US); Foster B. Stulen, Johns Island, SC (US); Frederick Estera, Cincinnati, OH (US); William E. Clem, Bozeman, MT (US); Jerome R. Morgan, Cincinnati, OH (US); Jeffrey L. Aldridge, Lebanon, OH (US); Stephen M. Leuck, Milford, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 1029 days.

(21) Appl. No.: 16/527,647

(22) Filed: Jul. 31, 2019

(65) Prior Publication Data

US 2019/0350615 A1  Nov. 21, 2019

Related U.S. Application Data

(62) Division of application No. 15/679,948, filed on Aug. 17, 2017, now Pat. No. 10,420,580.
(Continued)

(51) Int. Cl.
*A61B 17/00* (2006.01)
*A61B 17/32* (2006.01)
(Continued)

(52) U.S. Cl.
CPC ............... *A61B 17/320068* (2013.01); *A61B 17/00234* (2013.01); *A61N 7/02* (2013.01);
(Continued)

(58) Field of Classification Search
CPC .................. A61B 17/320068; A61B 17/00234
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| CA | 837241 A | 3/1970 |
|---|---|---|
| CA | 2535467 A1 | 4/1993 |

(Continued)

OTHER PUBLICATIONS

Technology Overview, printed from www.harmonicscalpel.com, Internet site, website accessed on Jun. 13, 2007, (3 pages).
(Continued)

*Primary Examiner* — Nicole F Lavert

(57) ABSTRACT

An ultrasonic surgical device is disclosed including a surgical tool including a proximal transducer mounting portion defining a surface, a distal end effector end, and a waveguide disposed therebetween, the waveguide extending along a longitudinal axis. The ultrasonic surgical device further includes a transducer is in mechanical communication with the surface of the transducer mounting portion. The transducer is configured to operate in a D31 mode with respect to the longitudinal axis of the waveguide. Upon activation by an electrical signal having a predetermined frequency component, the transducer is configured to induce a standing wave in the surgical tool to cause the end effector to vibrate, the standing wave having a wavelength proportional to the predetermined frequency component of the electrical signal.

8 Claims, 31 Drawing Sheets

Related U.S. Application Data

(60) Provisional application No. 62/379,550, filed on Aug. 25, 2016.

(51) Int. Cl.
  A61N 7/02 (2006.01)
  B29C 65/48 (2006.01)
  H10N 30/20 (2023.01)
  H10N 30/50 (2023.01)
  H10N 30/88 (2023.01)
  A61B 17/16 (2006.01)
  A61B 17/22 (2006.01)
  A61B 17/29 (2006.01)
  A61B 18/00 (2006.01)
  B29L 31/00 (2006.01)

(52) U.S. Cl.
  CPC ....... *B29C 65/4805* (2013.01); *H10N 30/206* (2023.02); *H10N 30/50* (2023.02); *H10N 30/505* (2023.02); *H10N 30/886* (2023.02); *A61B 2017/00017* (2013.01); *A61B 2017/00402* (2013.01); *A61B 2017/00477* (2013.01); *A61B 2017/00526* (2013.01); *A61B 2017/0088* (2013.01); *A61B 17/1628* (2013.01); *A61B 2017/22027* (2013.01); *A61B 2017/294* (2013.01); *A61B 2017/32007* (2017.08); *A61B 2017/320074* (2017.08); *A61B 2017/320082* (2017.08); *A61B 2017/320088* (2013.01); *A61B 2017/320089* (2017.08); *A61B 2017/320098* (2017.08); *A61B 2018/00565* (2013.01); *A61B 2018/00589* (2013.01); *A61B 2018/00595* (2013.01); *B29L 2031/7546* (2013.01); *Y10T 29/42* (2015.01)

(58) Field of Classification Search
  USPC ......................................................... 606/169
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,057,660 A | 11/1977 | Yoshida et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,169,984 A | 10/1979 | Parisi |
| 4,173,725 A | 11/1979 | Asai et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Helges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,352,459 A | 10/1982 | Berger et al. |
| 4,445,063 A | 4/1984 | Smith |
| 4,452,473 A | 6/1984 | Ruschke |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |

(56) References Cited

U.S. PATENT DOCUMENTS

| | | |
|---|---|---|
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,696,667 A | 9/1987 | Masch |
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,783,997 A | 11/1988 | Lynnworth |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | Mcgurk-Burleson et al. |
| 4,852,578 A | 8/1989 | Companion et al. |
| 4,860,745 A | 8/1989 | Farin et al. |
| 4,861,332 A | 8/1989 | Parisi |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,978,067 A | 12/1990 | Berger et al. |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,057,119 A | 10/1991 | Clark et al. |
| 5,058,570 A | 10/1991 | Idemoto et al. |
| 5,059,210 A | 10/1991 | Clark et al. |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,613 A | 10/1992 | Sawyer |
| 5,156,633 A | 10/1992 | Smith |
| 5,159,226 A | 10/1992 | Montgomery |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,209,776 A | 5/1993 | Bass et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,385 A | 9/1993 | Strukel |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,289,436 A | 2/1994 | Terhune |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| 5,306,280 A | 4/1994 | Bregen et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,327 A | 5/1994 | Bales et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,297 A | 6/1994 | Hood et al. |
| 5,324,299 A | 6/1994 | Davison et al. |
| 5,326,013 A | 7/1994 | Green et al. |

(56) References Cited

U.S. PATENT DOCUMENTS

| | | |
|---|---|---|
| 5,326,342 A | 7/1994 | Pflueger et al. |
| 5,330,471 A | 7/1994 | Eggers |
| 5,330,502 A | 7/1994 | Hassler et al. |
| 5,338,292 A | 8/1994 | Clement et al. |
| 5,339,723 A | 8/1994 | Huitema |
| 5,342,292 A | 8/1994 | Nita et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,356,064 A | 10/1994 | Green et al. |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,372,585 A | 12/1994 | Tiefenbrun et al. |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,883 A | 1/1995 | Wilk et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,397,293 A | 3/1995 | Alliger et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,413,107 A | 5/1995 | Oakley et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,496,411 A | 3/1996 | Candy |
| 5,499,992 A | 3/1996 | Meade et al. |
| 5,500,216 A | 3/1996 | Julian et al. |
| 5,501,654 A | 3/1996 | Failla et al. |
| 5,503,616 A | 4/1996 | Jones |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,273 A | 6/1996 | Manna et al. |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,575,799 A | 11/1996 | Bolanos et al. |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tai et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,578 A | 5/1997 | Tihon |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,851 A | 7/1997 | Pokras |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |

(56) References Cited

U.S. PATENT DOCUMENTS

| | | |
|---|---|---|
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,725,536 A | 3/1998 | Oberlin et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,735,875 A | 4/1998 | Bonutti et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,537 A | 8/1998 | Oberlin et al. |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,310 A | 9/1998 | Hood |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,810,869 A | 9/1998 | Kaplan et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,820,009 A | 10/1998 | Melling et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,290 A | 12/1998 | Winston |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,363 A | 3/1999 | Urich |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,893,880 A | 4/1999 | Egan et al. |
| 5,895,412 A | 4/1999 | Tucker |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,910,150 A | 6/1999 | Saadat |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,941,887 A | 8/1999 | Steen et al. |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,010,054 A | 1/2000 | Johnson et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,053,906 A | 4/2000 | Honda et al. |
| 6,056,735 A | 5/2000 | Okada et al. |
| 6,063,050 A | 5/2000 | Manna et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,544 A | 7/2000 | Hibner et al. |

(56) References Cited

U.S. PATENT DOCUMENTS

| | | |
|---|---|---|
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,217,591 B1 | 4/2001 | Egan et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,471 B1 | 8/2001 | Hechel et al. |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| 6,409,743 B1 | 6/2002 | Fenton, Jr. |
| H2037 H | 7/2002 | Yates et al. |
| 6,416,469 B1 | 7/2002 | Phung et al. |
| 6,416,486 B1 | 7/2002 | Wampler |
| 6,416,525 B1 | 7/2002 | Shibata |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 | 7/2002 | Shibata et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |

(56) References Cited

U.S. PATENT DOCUMENTS

| | | |
|---|---|---|
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,498,421 B1 | 12/2002 | Oh et al. |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,526,976 B1 | 3/2003 | Baran |
| 6,527,736 B2 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,562,059 B2 | 5/2003 | Edwards et al. |
| 6,565,558 B1 | 5/2003 | Lindenmeier et al. |
| 6,569,109 B2 | 5/2003 | Sakurai et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,929 B2 | 6/2003 | Sussman et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,229 B2 | 8/2003 | Coss |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,444 B2 | 9/2003 | Babaev |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,839 B2 | 11/2003 | Manna et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,124 B2 | 12/2003 | Flesch et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,086 B1 | 2/2004 | Nita et al. |
| 6,689,145 B2 | 2/2004 | Lee et al. |
| 6,689,146 B1 | 2/2004 | Himes |
| 6,690,960 B2 | 2/2004 | Chen et al. |
| 6,692,514 B2 | 2/2004 | Fogarty et al. |
| 6,695,782 B2 | 2/2004 | Ranucci et al. |
| 6,695,840 B2 | 2/2004 | Schulze |
| 6,699,214 B2 | 3/2004 | Gellman |
| 6,702,761 B1 | 3/2004 | Damadian et al. |
| 6,702,821 B2 | 3/2004 | Bonutti |
| 6,712,805 B2 | 3/2004 | Weimann |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |

(56) References Cited

U.S. PATENT DOCUMENTS

| | | | |
|---|---|---|---|
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,832,988 B2 | 12/2004 | Sproul |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,221 B1 | 5/2005 | Baillargeon et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,466 B1 | 6/2005 | Bonutti et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,932,876 B1 | 8/2005 | Statnikov |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,989,017 B2 | 1/2006 | Howell et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,354 B2 | 3/2006 | Tazi |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,062,314 B2 | 6/2006 | Zhu et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,036 B1 | 7/2006 | Adams |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,131,983 B2 | 11/2006 | Murakami |
| 7,135,018 B2 | 11/2006 | Ryan et al. |
| 7,135,029 B2 | 11/2006 | Makin et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,182,762 B2 | 2/2007 | Bortkiewicz |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |

(56) References Cited

U.S. PATENT DOCUMENTS

| | | |
|---|---|---|
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,338,463 B2 | 3/2008 | Vigil |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,533,830 B1 | 5/2009 | Rose |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,627,936 B2 | 12/2009 | Bromfield |
| 7,628,791 B2 | 12/2009 | Garrison et al. |
| 7,628,792 B2 | 12/2009 | Guerra |

(56) References Cited

U.S. PATENT DOCUMENTS

| | | |
|---|---|---|
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,763 B2 | 3/2010 | Vaezy et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,670 B2 | 4/2010 | Sakamoto |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,785,324 B2 | 8/2010 | Eberl |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,815,658 B2 | 10/2010 | Murakami |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,834,521 B2 | 11/2010 | Habu et al. |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,465 B2 | 2/2011 | Donofrio et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,716 B2 | 4/2011 | Malecki et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |

(56) References Cited

U.S. PATENT DOCUMENTS

| | | |
|---|---|---|
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,006,358 B2 | 8/2011 | Cooke et al. |
| 8,016,843 B2 | 9/2011 | Escaf |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,011 B2 | 11/2011 | Okabe |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Esky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,137,263 B2 | 3/2012 | Marescaux et al. |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,353,847 B2 | 1/2013 | Kuhns et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,096 B2 | 3/2013 | Moses et al. |

(56) References Cited

U.S. PATENT DOCUMENTS

| | | |
|---|---|---|
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,435,258 B2 | 5/2013 | Young et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,610,334 B2 | 12/2013 | Bromfield |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,691,268 B2 | 4/2014 | Weimann |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |

(56) References Cited

U.S. PATENT DOCUMENTS

| | | |
|---|---|---|
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,023,072 B2 | 5/2015 | Young et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |

(56) References Cited

U.S. PATENT DOCUMENTS

| | | |
|---|---|---|
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horiie et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |

(56) References Cited

U.S. PATENT DOCUMENTS

| | | |
|---|---|---|
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,561,436 B2 | 2/2020 | Asher et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,603,064 B2 | 3/2020 | Zhang |
| 10,610,286 B2 | 4/2020 | Wiener et al. |
| 10,624,665 B2 | 4/2020 | Noui et al. |
| 10,624,691 B2 | 4/2020 | Wiener et al. |
| 10,639,092 B2 | 5/2020 | Corbett et al. |
| 10,646,267 B2 | 5/2020 | Ding |
| 10,677,764 B2 | 6/2020 | Ross et al. |
| 10,687,884 B2 | 6/2020 | Wiener et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,261 B2 | 7/2020 | Houser et al. |
| 10,729,458 B2 | 8/2020 | Stoddard et al. |
| 10,736,649 B2 | 8/2020 | Messerly et al. |
| 10,736,685 B2 | 8/2020 | Wiener et al. |
| 10,751,108 B2 | 8/2020 | Yates et al. |
| 10,758,294 B2 | 9/2020 | Jones |
| 10,779,845 B2 | 9/2020 | Timm et al. |
| 10,779,847 B2 | 9/2020 | Messerly et al. |
| 10,779,848 B2 | 9/2020 | Houser |
| 10,779,849 B2 | 9/2020 | Shelton, IV et al. |
| 10,779,879 B2 | 9/2020 | Yates et al. |
| 10,820,920 B2 | 11/2020 | Scoggins et al. |
| 10,820,938 B2 | 11/2020 | Fischer et al. |
| 10,828,056 B2 | 11/2020 | Messerly et al. |
| 10,828,057 B2 | 11/2020 | Neurohr et al. |
| 10,828,058 B2 | 11/2020 | Shelton, IV et al. |
| 10,828,059 B2 | 11/2020 | Price et al. |
| 10,835,307 B2 | 11/2020 | Shelton, IV et al. |
| 10,835,768 B2 | 11/2020 | Robertson et al. |
| 10,842,522 B2 | 11/2020 | Messerly et al. |
| 10,842,523 B2 | 11/2020 | Shelton, IV et al. |
| 10,842,580 B2 | 11/2020 | Gee et al. |
| 10,856,896 B2 | 12/2020 | Eichmann et al. |
| 10,874,418 B2 | 12/2020 | Houser et al. |

(56) References Cited

U.S. PATENT DOCUMENTS

| | | |
|---|---|---|
| 10,881,449 B2 | 1/2021 | Boudreaux et al. |
| 10,881,451 B2 | 1/2021 | Worrell et al. |
| 10,888,347 B2 | 1/2021 | Witt et al. |
| 10,893,883 B2 | 1/2021 | Dannaher |
| 10,912,603 B2 | 2/2021 | Boudreaux et al. |
| 10,952,759 B2 | 3/2021 | Messerly et al. |
| 10,959,769 B2 | 3/2021 | Mumaw et al. |
| 10,966,744 B2 | 4/2021 | Rhee et al. |
| 10,987,123 B2 | 4/2021 | Weir et al. |
| 11,000,707 B2 | 5/2021 | Voegele et al. |
| 11,006,971 B2 | 5/2021 | Faller et al. |
| 11,020,140 B2 | 6/2021 | Gee et al. |
| 11,033,292 B2 | 6/2021 | Green et al. |
| 11,033,322 B2 | 6/2021 | Wiener et al. |
| D924,400 S | 7/2021 | Kimball |
| 11,051,840 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,129,670 B2 | 9/2021 | Shelton, IV et al. |
| 11,134,978 B2 | 10/2021 | Shelton, IV et al. |
| 11,141,213 B2 | 10/2021 | Yates et al. |
| 11,690,643 B2 | 7/2023 | Witt et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0032002 A1 | 10/2001 | McClurken et al. |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0099373 A1 | 7/2002 | Schulze et al. |
| 2002/0107446 A1 | 8/2002 | Rabiner et al. |
| 2002/0107517 A1 | 8/2002 | Witt et al. |
| 2002/0120266 A1 | 8/2002 | Truckai et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0120306 A1 | 6/2003 | Burbank et al. |
| 2003/0130675 A1 | 7/2003 | Kasahara et al. |
| 2003/0130693 A1 | 7/2003 | Levin et al. |
| 2003/0139741 A1 | 7/2003 | Goble et al. |
| 2003/0144652 A1 | 7/2003 | Baker et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0195496 A1 | 10/2003 | Maguire et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212391 A1 | 11/2003 | Fenton et al. |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0085728 A1 | 4/2005 | Fukuda |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0228425 A1 | 10/2005 | Boukhny et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0025802 A1 | 2/2006 | Sowers |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |

(56) References Cited

U.S. PATENT DOCUMENTS

| | | |
|---|---|---|
| 2006/0100652 A1 | 5/2006 | Beaupre |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0241580 A1 | 10/2006 | Mittelstein et al. |
| 2006/0247558 A1 | 11/2006 | Yamada |
| 2006/0253050 A1 | 11/2006 | Yoshimine et al. |
| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0198005 A1 | 8/2007 | Ichihashi et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0276419 A1 | 11/2007 | Rosenthal |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0234711 A1* | 9/2008 | Houser ......... A61B 17/320068 606/169 |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0294051 A1 | 11/2008 | Koshigoe et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1* | 3/2009 | Mulvihill ....... A61B 17/320068 606/171 |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0234906 A1 | 9/2010 | Koh |

(56) References Cited

U.S. PATENT DOCUMENTS

| | | |
|---|---|---|
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0078249 A1 | 3/2012 | Eichmann et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116363 A1 | 5/2012 | Houser et al. |
| 2012/0136279 A1 | 5/2012 | Tanaka et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2012/0330338 A1 | 12/2012 | Messerly |
| 2013/0023925 A1 | 1/2013 | Mueller |
| 2013/0072948 A1 | 3/2013 | States, III et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0197511 A1 | 8/2013 | Balanev et al. |
| 2013/0231691 A1 | 9/2013 | Houser |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0331873 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005701 A1* | 1/2014 | Olson ............ A61B 17/320068 606/206 |
| 2014/0005702 A1 | 1/2014 | Timm et al. |
| 2014/0005704 A1* | 1/2014 | Vakharia .............. A61B 17/295 606/169 |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0276963 A1 | 9/2014 | Ranucci et al. |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0083774 A1 | 3/2015 | Measamer et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0165240 A1 | 6/2015 | Stoddard et al. |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0114355 A1 | 4/2016 | Sakai et al. |
| 2016/0128769 A1 | 5/2016 | Rontal et al. |
| 2016/0175029 A1 | 6/2016 | Witt et al. |
| 2016/0206342 A1 | 7/2016 | Robertson et al. |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2017/0027624 A1 | 2/2017 | Wilson et al. |
| 2017/0036044 A1 | 2/2017 | Ito |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0202572 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202598 A1 | 7/2017 | Shelton, IV et al. |
| 2017/0205234 A1 | 7/2017 | Honda |
| 2018/0055529 A1 | 3/2018 | Messerly et al. |
| 2018/0125523 A1 | 5/2018 | Johnson |
| 2019/0053822 A1 | 2/2019 | Robertson et al. |
| 2019/0239919 A1 | 8/2019 | Witt et al. |
| 2019/0262029 A1 | 8/2019 | Messerly et al. |
| 2019/0380733 A1 | 12/2019 | Stulen et al. |
| 2019/0381340 A1 | 12/2019 | Voegele et al. |
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085462 A1 | 3/2020 | Robertson |
| 2020/0085466 A1 | 3/2020 | Faller et al. |
| 2020/0323551 A1 | 10/2020 | Faller et al. |
| 2021/0038248 A1 | 2/2021 | Houser |
| 2021/0121197 A1 | 4/2021 | Houser et al. |
| 2021/0128191 A1 | 5/2021 | Messerly et al. |
| 2021/0145531 A1 | 5/2021 | Gee et al. |
| 2021/0236157 A1 | 8/2021 | Rhee et al. |
| 2021/0315605 A1 | 10/2021 | Gee et al. |
| 2021/0378700 A1 | 12/2021 | Houser |
| 2022/0257276 A1 | 8/2022 | Robertson |
| 2022/0346824 A1 | 11/2022 | Messerly et al. |
| 2023/0191161 A1 | 6/2023 | Wiener et al. |

FOREIGN PATENT DOCUMENTS

| | | |
|---|---|---|
| CA | 2214413 A1 | 9/1996 |
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| CN | 106077718 A | 11/2016 |

(56) References Cited

FOREIGN PATENT DOCUMENTS

| | | |
|---|---|---|
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1543854 A1 | 6/2005 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2454351 A1 | 11/1980 |
| FR | 2964554 A1 | 3/2012 |
| GB | 2032221 A | 4/1980 |
| GB | 2317566 A | 4/1998 |
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H04161078 A | 6/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H07185457 A | 7/1995 |
| JP | H07299415 A | 11/1995 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210296 A | 8/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2001057985 A | 3/2001 |
| JP | 2001170066 A | 6/2001 |
| JP | 2001198137 A | 7/2001 |
| JP | 2002035002 A | 2/2002 |
| JP | 2002186901 A | 7/2002 |
| JP | 2002233533 A | 8/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003230567 A | 8/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | 3841627 B2 | 11/2006 |
| JP | 2007177931 A | 7/2007 |
| JP | D1339835 S | 8/2008 |
| JP | 2009071439 A | 4/2009 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| JP | 2014121340 A | 7/2014 |
| JP | 2015529140 A | 10/2015 |
| JP | 2016022136 A | 2/2016 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9805437 A1 | 2/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0132087 A1 | 5/2001 |
| WO | WO-0167970 A1 | 9/2001 |
| WO | WO-0195810 A2 | 12/2001 |
| WO | WO-02076685 A1 | 10/2002 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2008154338 A1 | 12/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |

(56) References Cited

FOREIGN PATENT DOCUMENTS

| WO | WO-2012044606 A2 | 4/2012 |
|---|---|---|
| WO | WO-2012066983 A1 | 5/2012 |
| WO | WO-2013048963 A2 | 4/2013 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191.asp (15 pages).
Covidien Brochure, The LigaSure Precise™ Instrument, dated Mar. 2011 (2 pages).
AST Products, Inc., "Principles of Video Contact Angle Analysis," 20 pages, (2006).
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.
Sadiq Muhammad et al.: "High-performance planar ultrasonic tool based on d31-mode piezocrystal", IEEE Transactions On Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Leonard I. Malis, M.D., "The Value of Irrigation During Bipolar Coagulation," 1989.
http:/www.ethicon.com/GB-en/healthcare-professionals/products/energy-devices/capital//ge . . . .
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al., "Thermal Imaging in Surgery," p. 19-3, in Medical Infrared Imaging, N. A. Diakides and J. D. Bronzino, Eds. (2008).
http://www.dotmed.com/listing/electrosurical-unit/ethicon/ultracision-g110-/1466724.
http://www.4-traders.com/JOHNSON-JOHNSON-4832/news/Johnson-Johnson-Ethicon-E . . . .
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).

(56) References Cited

OTHER PUBLICATIONS

National Semiconductors Temperature Sensor Handbook—http://www.national.com/appinfo/tempsensors/files/temphb.pdf; accessed online: Apr. 1, 2011.

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Douglas, S.C. "Introduction to Adaptive Filter". Digital Signal Processing Handbook. Ed. Vijay K. Madisetti and Douglas B. Williams. Boca Raton: CRC Press LLC, 1999.

Chen et al., "Heat-induced changes in the mechanics of a collagenous tissue: pseudoelastic behavior at 37° C.," Journal of Biomechanics, 31, pp. 211-216 (1998).

Kurt Gieck & Reiner Gieck, *Engineering Formulas* § Z.7 (7th ed. 1997).

Glaser and Subak-Sharpe,Integrated Circuit Engineering, Addison-Wesley Publishing, Reading, MA (1979). (book—not attached).

Covidien 501 (k) Summary Sonicision, dated Feb. 24, 2011 (7 pages).

http://www.megadyne.com/es_generator.php.

Lacourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

http://www.apicalinstr.com/generators.htm.

http://www.medicalexpo.com/medical-manufacturer/electrosurgical-generator-6951.html.

http://www.valleylab.com/product/es/generators/index.html.

Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.

Fell, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).

McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.

\* cited by examiner

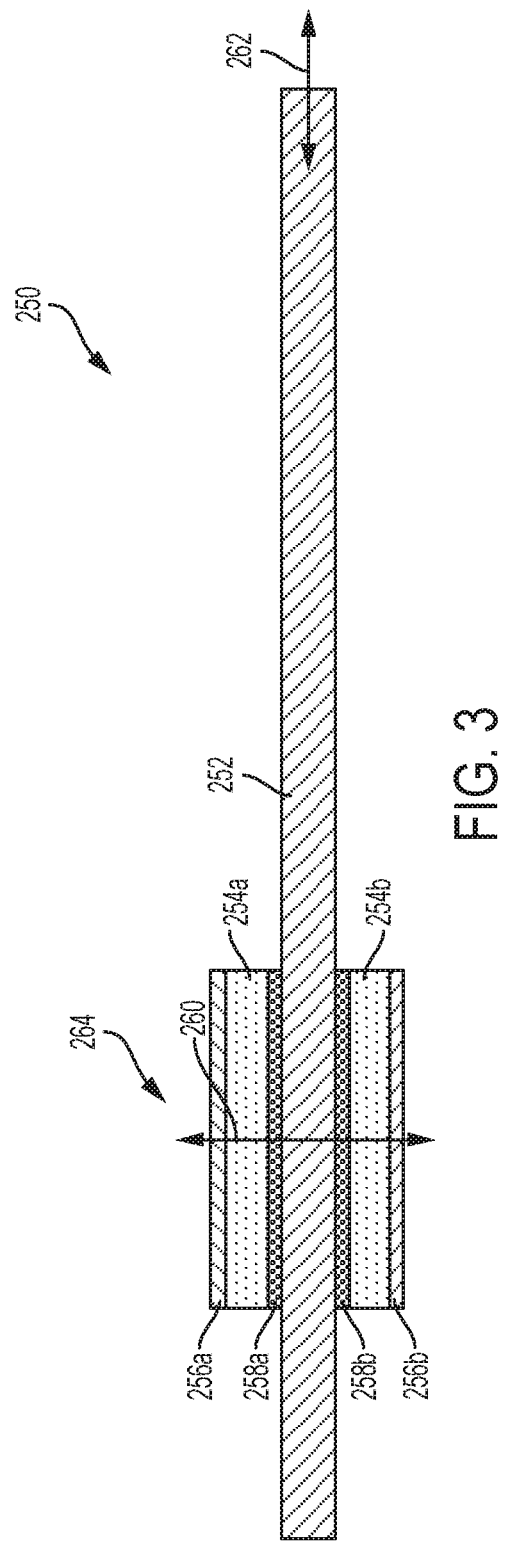

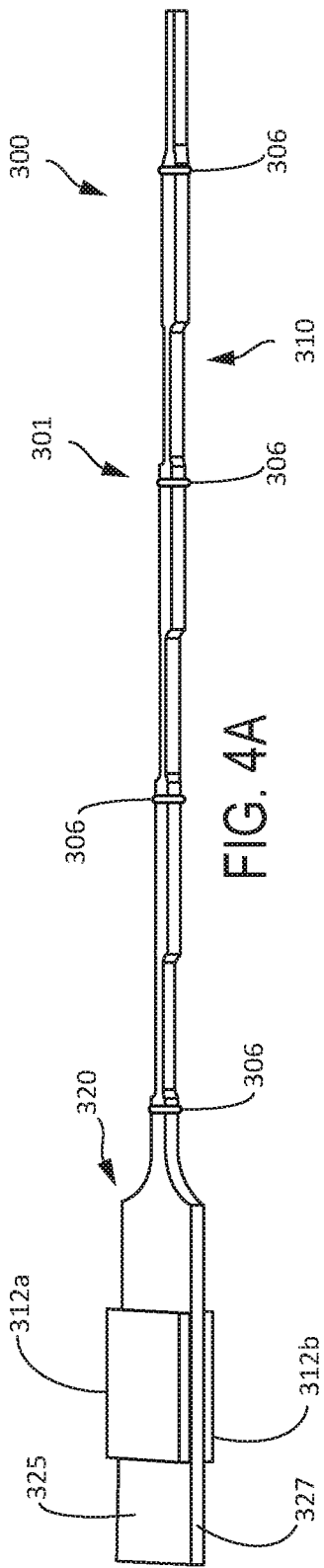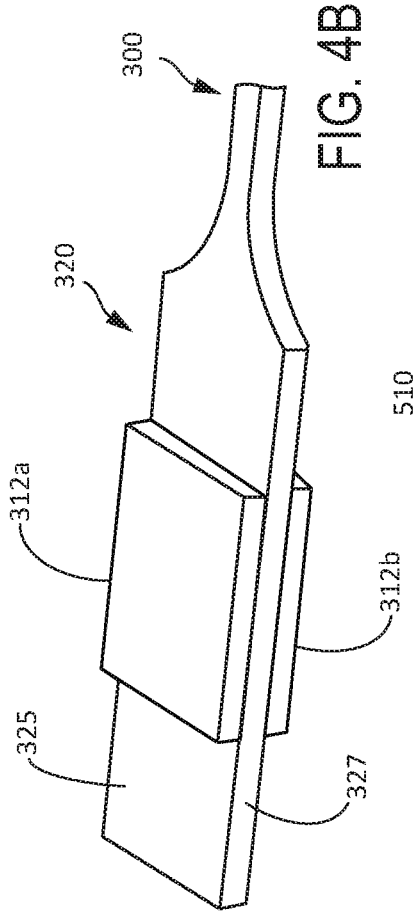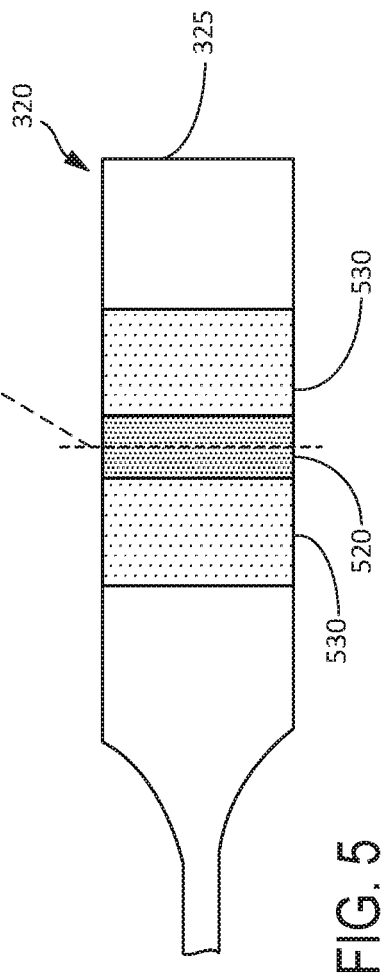
FIG. 4A
FIG. 4B
FIG. 5

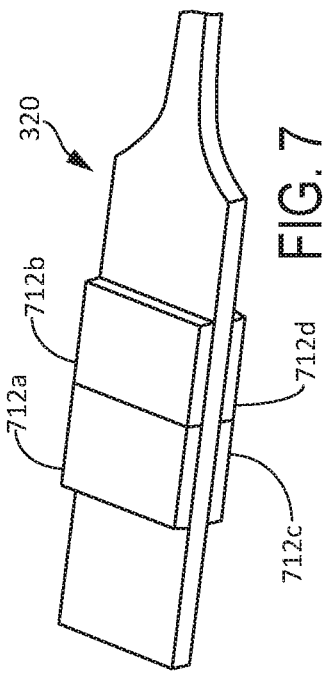
FIG. 6
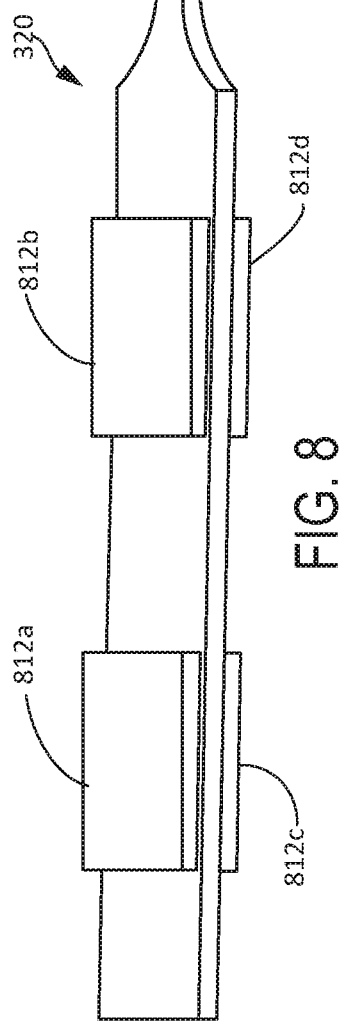
FIG. 7
FIG. 8
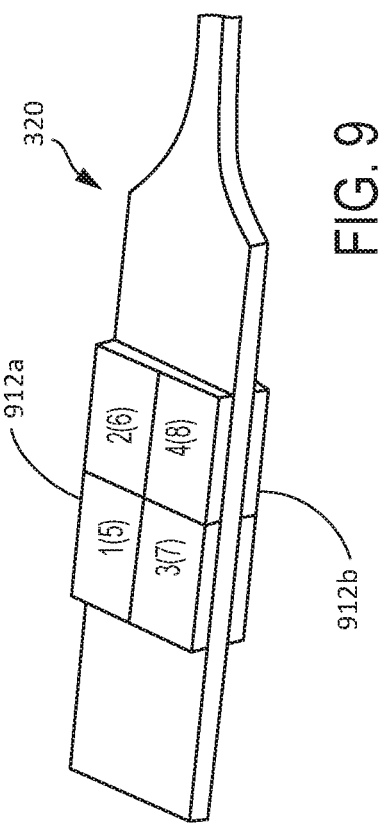
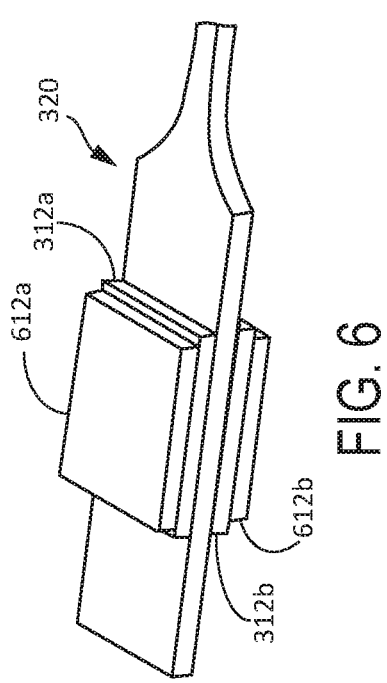
FIG. 9

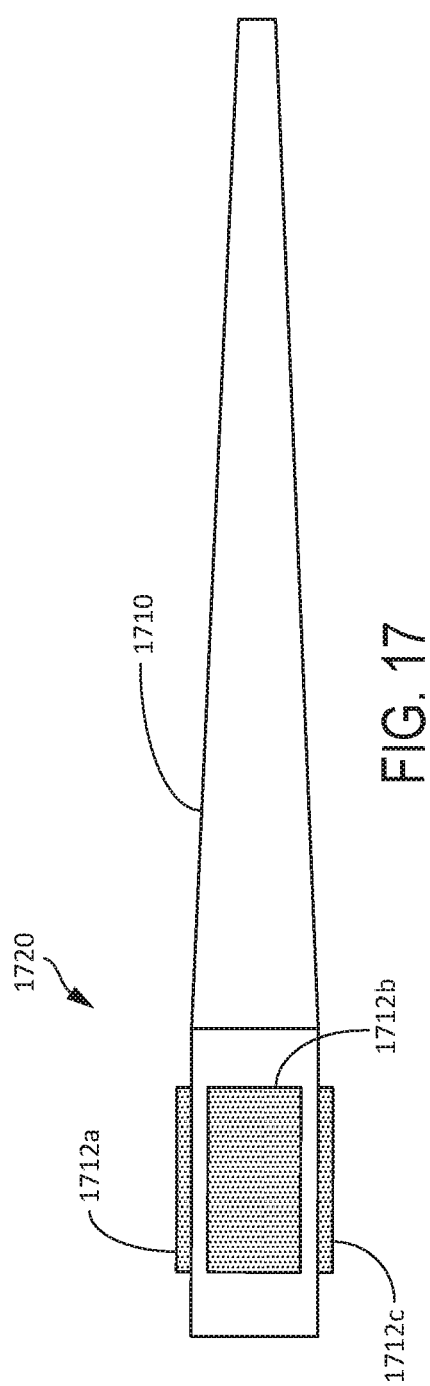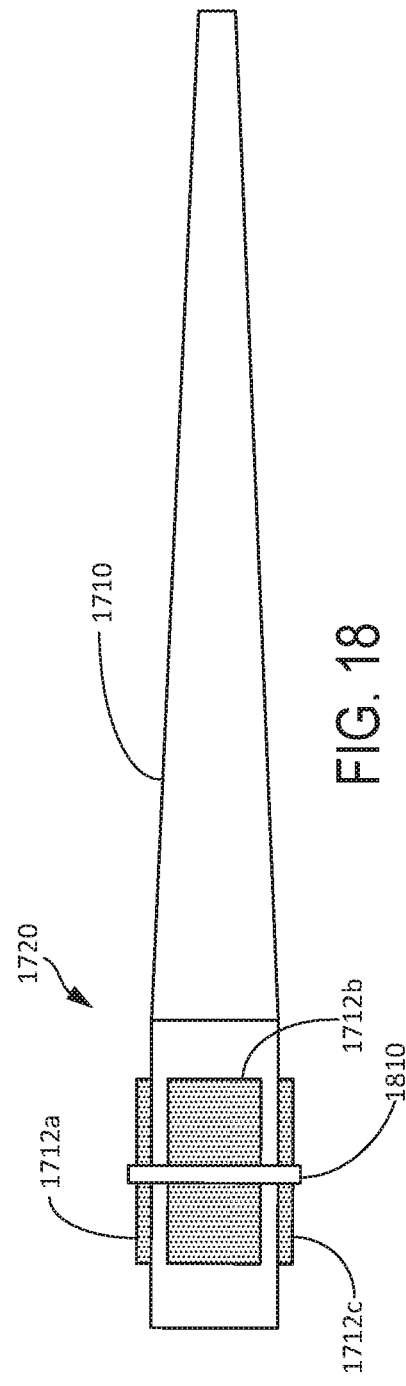

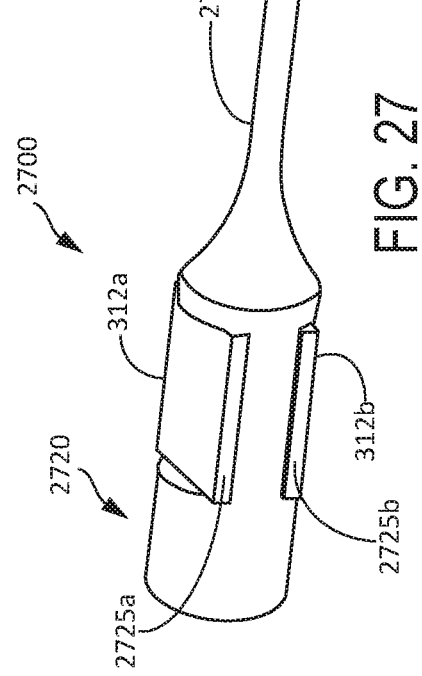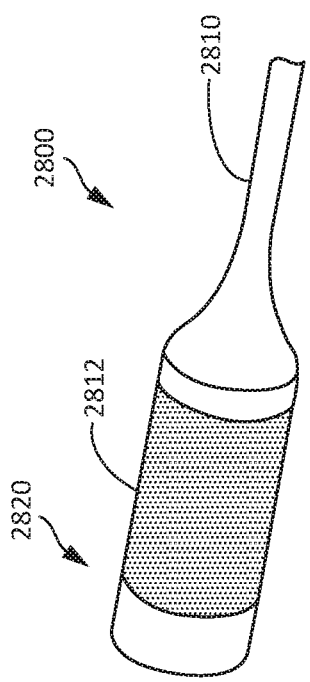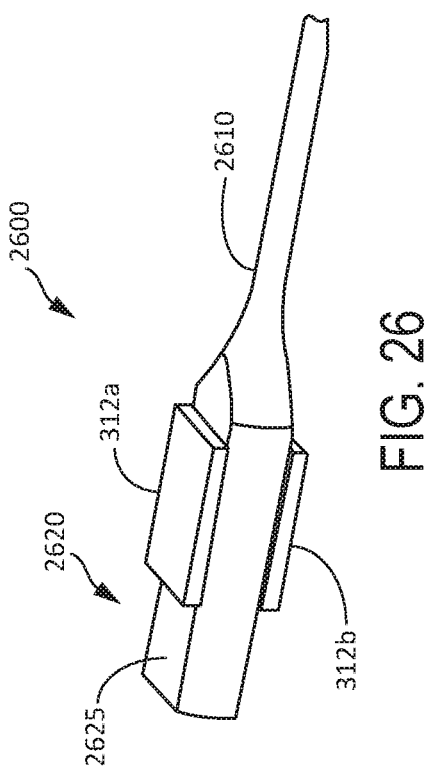

ULTRASONIC TRANSDUCER FOR SURGICAL INSTRUMENT

PRIORITY

This application is a divisional application claiming priority under 35 U.S.C. § 121 to U.S. Pat. No. 10,420,580, which issued on Sep. 24, 2019 and is entitled ULTRASONIC TRANSDUCER FOR SURGICAL INSTRUMENT, which claims the benefit of priority under 35 U.S.C. § 119(e) to U.S. Provisional Patent Application Ser. No. 62/379,550, entitled ULTRASONIC TRANSDUCER FOR SURGICAL INSTRUMENT, filed Aug. 25, 2016, the entire disclosures of which are hereby incorporated by reference herein.

BACKGROUND

The present disclosure relates, in general, to ultrasonic surgical instruments and more particularly to ultrasonic transducers to drive ultrasonic blades. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.

The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC BLADE HAVING A TRAPEZOIDAL CROSS SECTION; and U.S. Pat. No. 6,436,115, which issued on Aug. 20, 2002 and is entitled BALANCED ULTRASONIC BLADE INCLUDING A PLURALITY OF BALANCE ASYMMETRIES, the entire disclosures of which are hereby incorporated by reference herein, disclose various ultrasonic surgical instruments.

SUMMARY

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic blade extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In one aspect, the present disclosure provides an ultrasonic medical device comprising a surgical tool comprising a transducer mounting portion (e.g., a transducer base plate) at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

In another aspect, the present disclosure provides an ultrasonic surgical device comprising a surgical tool comprising a proximal transducer mounting portion defining a surface, a distal end effector end, and a waveguide disposed therebetween, the waveguide extending along a longitudinal axis; and a transducer in mechanical communication with the surface of the transducer mounting portion; wherein the transducer is configured to operate in a D31 mode with respect to the longitudinal axis of the waveguide; and wherein, upon activation by an electrical signal having a predetermined frequency component, the transducer is configured to induce a standing wave in the surgical tool to cause the end effector to vibrate, the standing wave having a wavelength proportional to the predetermined frequency component of the electrical signal.

In another aspect, the present disclosure provides an ultrasonic medical device comprising: a surgical tool comprising a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; a third transducer comprising a body defining a face; and a fourth transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 3 illustrates a D31 ultrasonic transducer architecture that includes an ultrasonic waveguide and one or more piezoelectric elements fixed to the ultrasonic waveguide, according to one aspect of this disclosure.

FIG. 4A is another perspective view of an ultrasonic medical device having a single pair of piezoelectric transducers, according to one aspect of this disclosure.

FIG. 4B is a perspective view of a transducer mounting portion of an ultrasonic medical device depicted in FIG. 4A, according to one aspect of this disclosure.

FIG. 5 is a plan view of a transducer mounting portion of an ultrasonic medical device depicted in FIG. 4A, according to one aspect of this disclosure.

FIGS. 6-9 are perspective views of a transducer mounting portion of an ultrasonic medical device having multiple pairs of piezoelectric transducers, according to one aspect of this disclosure.

FIGS. 17 and 18 are plan views of an ultrasonic medical device having a transducer mounting portion having a form of a square or rectangular prism, according to one aspect of this disclosure.

FIGS. 26-28 are perspective views of an ultrasonic medical device fabricated from round stock, according to one aspect of this disclosure.

DESCRIPTION

Figure 1:
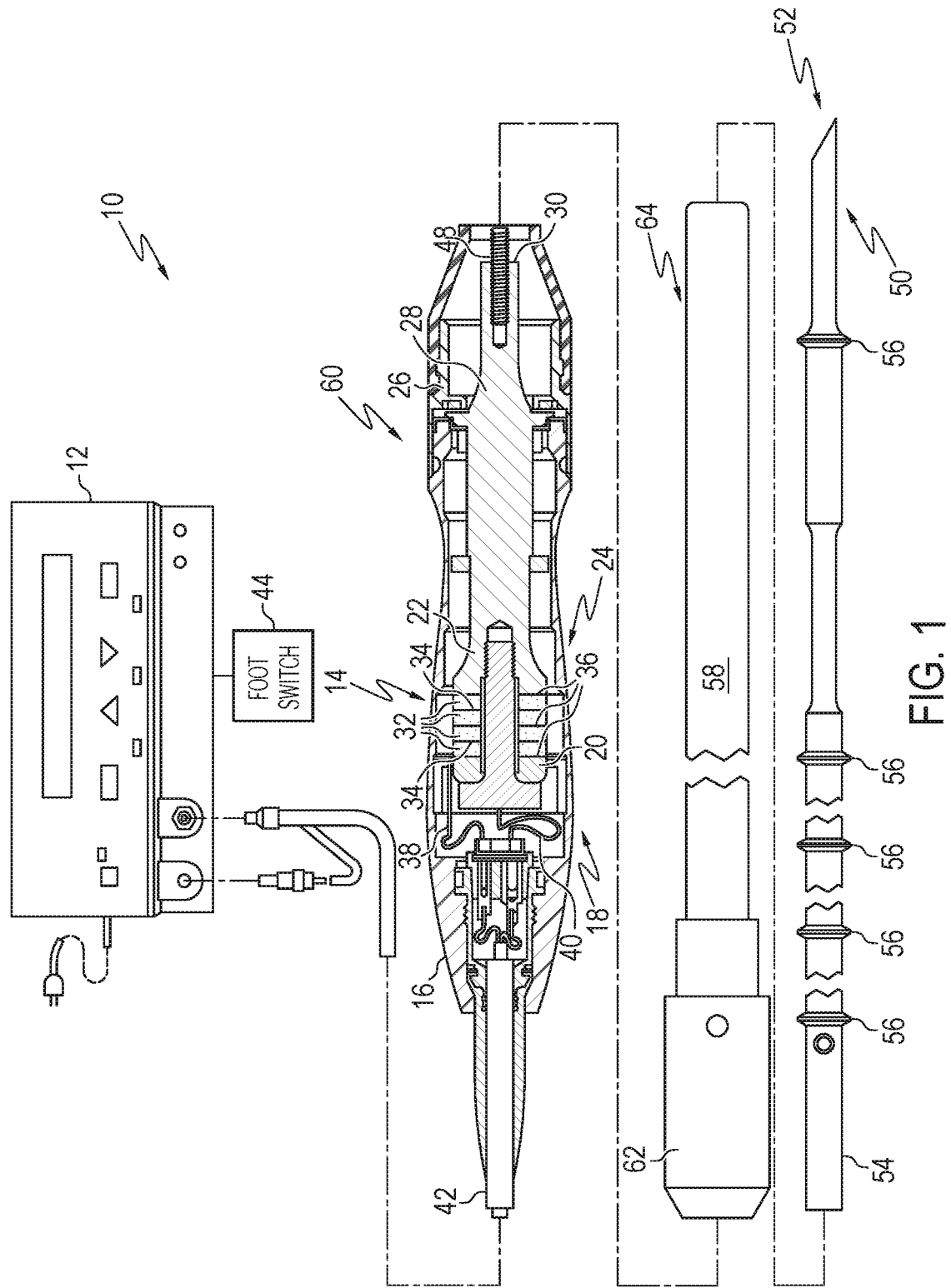
FIG. 1 illustrates an ultrasonic surgical instrument system, according to one aspect of this disclosure.

Applicant of the present application owns the following patent applications filed on Aug. 17, 2017 and which are each herein incorporated by reference in their respective entireties:

U.S. patent application Ser. No. 15/679,940, entitled ULTRASONIC TRANSDUCER TECHNIQUES FOR ULTRASONIC SURGICAL INSTRUMENT by inventors Jeffrey Messerly et al. filed Aug. 17, 2017.

U.S. patent application Ser. No. 15/679,952, ENTITLED ELECTRICAL AND THERMAL CONNECTIONS FOR ULTRASONIC TRANSDUCER by inventors Jeffrey Messerly et al. filed Aug. 17, 2017.

U.S. patent application Ser. No. 15/679,959, entitled ULTRASONIC TRANSDUCER TO WAVEGUIDE ACOUSTIC COUPLING, CONNECTIONS, AND CONFIGURATIONS by inventors Jeffrey Messerly et al. filed Aug. 17, 2017.

U.S. patent application Ser. No. 15/679,960, entitled ULTRASONIC TRANSDUCER TO WAVEGUIDE JOINING by inventors Jeffrey Messerly et al. filed Aug. 17, 2017.

U.S. patent application Ser. No. 15/679,967, entitled TISSUE LOADING OF A SURGICAL INSTRUMENT by inventors Jeffrey Messerly et al. filed Aug. 17, 2017.

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain exemplary aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various aspects is defined solely by the claims. The features illustrated or described in connection with one exemplary aspect may be combined with the features of other aspects. Such modifications and variations are intended to be included within the scope of the claims.

Various aspects described herein relate, in general, to ultrasonic surgical instruments and blades for use therewith. Examples of ultrasonic surgical instruments and blades are disclosed in U.S. Pat. Nos. 5,322,055; 5,954,736; 6,309,400;

6,278,218; 6,283,981; 6,325,811; and 8,319,400, wherein the entire disclosures of which are incorporated by reference herein.

According to various aspects, an ultrasonic instrument comprising a surgical tool having an end effector such as a blade can yield a particular benefit or benefits in orthopedic procedures where it is desirable to remove cortical bone and/or tissue while controlling bleeding. Due to its cutting and coagulation characteristics, a blade of an ultrasonic surgical instrument may be useful for general soft tissue cutting and coagulation. In certain circumstances, a blade according to various aspects may be useful to simultaneously cut and hemostatically seal or cauterize tissue. A blade may be straight or curved, and useful for either open or laparoscopic applications. A blade according to various aspects may be useful in spine surgery, especially to assist in posterior access in removing muscle from bone.

FIG. 1 illustrates one aspect of an ultrasonic system 10. One aspect of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack," generally includes a transduction portion 18, a first resonator or end-bell 20, and a second resonator or fore-bell 22, and ancillary components. In various aspects, the ultrasonic transducer 14 is preferably an integral number of one-half system wavelengths (nλ/2) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no tapering.

Referring again to FIG. 1, end-bell 20 can include a threaded member extending therefrom which can be configured to be threadably engaged with a threaded aperture in fore-bell 22. In various aspects, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead metaniobate, lead titanate, and/or any suitable piezoelectric crystal material, for example.

In various aspects, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various aspects, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various aspects, the ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN11, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength (λ/4).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various aspects, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths (λ/2). A distal end 52 of the ultrasonic end effector 50 may be disposed at, or at least near, an antinode in order to provide the maximum, or at least nearly maximum, longitudinal excursion of the distal end. When the transducer assembly is energized, in various aspects, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various aspects, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths (λ/2), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In the aspect illustrated in FIG. 1, the ultrasonic transmission waveguide 46 comprises a proximal portion 54 and a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various aspects, the sheath 58 may be threaded or snapped onto the distal end of the housing 16. In at least one aspect, the ultrasonic transmission waveguide 46 extends through the opening of the tubular member 64 and the silicone rings 56 can contact the sidewalls of the opening and isolate the ultrasonic transmission waveguide 46 therein. In various aspects, the adapter 62 of the sheath 58 is preferably constructed from Ultem®, for example, and the tubular member 64 is fabricated from stainless steel, for example. In at least one aspect, the ultrasonic transmission waveguide 46 may have polymeric material, for example, surrounding it in order to isolate it from outside contact.

As described above, a voltage, or power source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various aspects, the voltage potential can be cycled at a frequency which is the same as, or nearly the same as, the resonant frequency of the system of components comprising transducer 14, wave guide 46, and end effector 50, for example. In various aspects, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

It may be recognized, in reference to the ultrasonic surgical instrument system 10 of FIG. 1, that multiple components may be required to couple the mechanical vibrations from the piezoelectric elements 32 through the wave guide 46 to the end effector 50. The additional acoustic elements comprising the acoustic assembly 24 may add additional manufacturing costs, fabrication steps, and complexity to the system. Disclosed below are aspects of an ultrasonic medical device that may require fewer components, manufacturing steps, and costs than the equivalent device illustrated in FIG. 1 and as disclosed above.

Again, referring to FIG. 1, the piezoelectric elements 32 are configured into a "Langevin" stack, in which the piezoelectric elements 32 and their activating electrodes 34 and 36 (together, transducer 14) are interleaved. The mechanical vibrations of the activated piezoelectric elements 32 propagate along the longitudinal axis of the transducer 14, and are coupled via the acoustic assembly 24 to the end of the waveguide 46. Such a mode of operation of a piezoelectric element is frequently described as the D33 mode of the element, especially for ceramic piezoelectric elements comprising, for example, lead zirconate-titanate, lead metaniobate, or lead titanate. The D33 mode of operation of a ceramic piezoelectric element is illustrated in FIGS. 2A-2C.

Figure 2A:
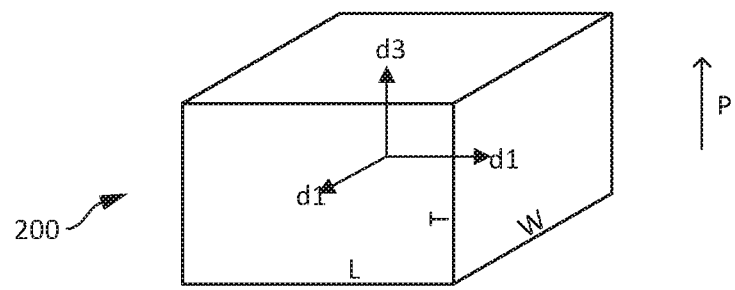
FIGS. 2A-2C illustrate a piezoelectric transducer, according to one aspect of this disclosure.

FIG. 2A depicts an exemplary piezoelectric element 200 fabricated from a ceramic piezoelectric material. A piezoelectric ceramic material is a polycrystalline material comprising a plurality of individual microcrystalline domains. Each microcrystalline domain possesses a polarization axis along which the domain may expand or contract in response to an imposed electric field. However, in a native ceramic, the polarization axes of the microcrystalline domains are arranged randomly, so there is no net piezoelectric effect in the bulk ceramic. A net re-orientation of the polarization axes may be induced by subjecting the ceramic to a temperature above the Currie temperature of the material and placing the material in a strong electrical field. Once the temperature of the sample is dropped below the Currie temperature, a majority of the individual polarization axes will be re-oriented and fixed in a bulk polarization direction. FIG. 2A illustrates such a piezoelectric element 200 after being polarized along the inducing electric field axis P. While the un-polarized piezoelectric element 200 lacks any net piezoelectric axis, the polarized element 200 can be described as possessing a polarization axis, d3, parallel to the inducing field axis P direction. For completeness, an axis orthogonal to the d3 axis may be termed a d1 axis. The dimensions of the piezoelectric element 200 are labeled as length (L), width (W), and thickness (T).

Figure 2B:
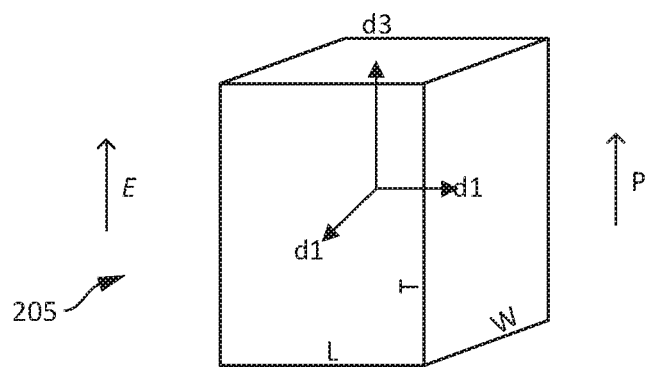
Figure 2C:
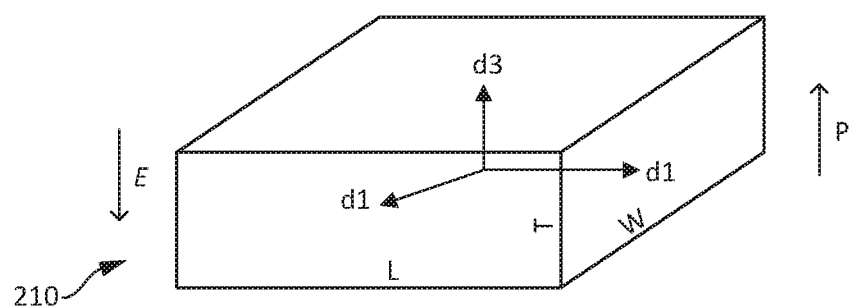

FIGS. 2B and 2C illustrate the mechanical deformations of a piezoelectric element 200 that may be induced by subjecting the piezoelectric element 200 to an actuating electrical field E oriented along the d3 (or P) axis. FIG. 2B illustrates the effect of an electric field E having the same direction as the polarization field P along the d3 axis on a piezoelectric element 205. As illustrated in FIG. 2B, the piezoelectric element 205 may deform by expanding along the d3 axis while compressing along the d1 axis. FIG. 2C illustrates the effect of an electric field E having the opposing direction to the polarization field P along the d3 axis on a piezoelectric element 210. As illustrated in FIG. 2C, the piezoelectric element 210 may deform by compressing along the d3 axis, while expanding along the d1 axis. Vibrational coupling along the d3 axis during the application of an electric field along the d3 axis may be termed D33 coupling or activation using a D33 mode of a piezoelectric element. The transducer 14 illustrated in FIG. 1 uses the D33 mode of the piezoelectric elements 32 for transmitting mechanical vibrations along the wave guide 46 to the end effector 50.

Because the piezoelectric elements 32 also deform along the d1 axis, vibrational coupling along the d1 axis during the application of an electric field along the d3 axis may also be an effective source of mechanical vibrations. Such coupling may be termed D31 coupling or activation using a D31 mode of a piezoelectric element. As illustrated by FIGS. 2A-2C, during operation in the D31 mode, transverse expansion of piezoelectric elements 200, 205, 210 may be mathematically modeled by the following equation:

$$\frac{\Delta L}{L} = \frac{\Delta W}{W} = \frac{V_{d31}}{T}$$

In the equation, L, W, and T refer to the length, width and thickness dimensions of a piezoelectric element, respectively. $Vd_{31}$ denotes the voltage applied to a piezoelectric element operating in the D31 mode. The quantity of transverse expansion resulting from the D31 coupling described above is represented by $\Delta L$ (i.e., expansion of the piezoelectric element along the length dimension) and $\Delta W$ (i.e., expansion of the piezoelectric element along the width dimension). Additionally, the transverse expansion equation models the relationship between $\Delta L$ and $\Delta W$ and the applied voltage $Vd_{31}$. Disclosed below are aspects of ultrasonic medical devices based on D31 activation by a piezoelectric element.

In various aspects, as described below, a ultrasonic medical device can comprise a transducer configured to produce longitudinal vibrations, and a surgical tool having a transducer mounting portion operably coupled to the transducer, an end effector, and wave guide therebetween. In certain aspects, as also described below, the transducer can produce vibrations which can be transmitted to the end effector, wherein the vibrations can drive the transducer mounting portion, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer mounting portion, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

FIG. 3 illustrates an ultrasonic surgical instrument 250 that includes an ultrasonic waveguide 252 attached to an ultrasonic transducer 264 by a bonding material, where the ultrasonic surgical instrument 250 is configured to operate in a D31 mode, according to one aspect of the present disclosure. The ultrasonic transducer 264 includes first and second piezoelectric elements 254a, 254b attached to the ultrasonic waveguide 252 by a bonding material. The piezoelectric elements 254a, 254b include electrically conductive plates 256a, 256b to electrically couple one pole of a voltage source suitable to drive the piezoelectric elements 254a, 254b (e.g., usually a high voltage). The opposite pole of the voltage source is electrically coupled to the ultrasonic waveguide 252 by electrically conductive joints 258a, 258b. In one aspect, the electrically conductive plates 256a, 256b are coupled to a positive pole of the voltage source and the electrically conductive joints 258a, 258b are electrically coupled to ground potential through the metal ultrasonic waveguide 252. In one aspect, the ultrasonic waveguide 252 is made of titanium or titanium alloy (i.e., Ti6Al4V) and the piezoelectric elements 254a, 254b are made of a lead zirconate titanate intermetallic inorganic compound with the chemical formula $Pb[Zr_xTi_{1-x}]O_3$ ($0 \leq x \leq 1$). Also called PZT, it is a ceramic perovskite material that shows a marked piezoelectric effect, meaning that the compound changes shape when an electric field is applied. It is used in a number of practical applications such as ultrasonic transducers and piezoelectric resonators PZT. The poling axis (P) of the piezoelectric elements 254a, 254b is indicated by the direction arrow 260. The motion axis of the ultrasonic waveguide 252 in response to excitation of the piezoelectric elements 254a, 245b is shown by a motion arrow 262 at the distal end of the ultrasonic waveguide 252 generally referred to as the ultrasonic blade portion of the ultrasonic waveguide 252. The motion axis 262 is orthogonal to the poling axis (P) 260.

In conventional D33 ultrasonic transducer architectures as shown in FIG. 1, the bolted piezoelectric elements 32 utilize electrodes 34, 36 to create electrical contact to both sizes of each piezoelectric element 34. The D31 architecture 250 according to one aspect of the present disclosure, however, employs a different technique to create electrical contact to both sides of each piezoelectric element 254a, 254b. Various techniques for providing electrical contact to the piezoelectric elements 254a, 254b include bonding electrical conductive elements (e.g., wires) to the free surface of each piezoelectric element 254a, 254b for the high potential connection and bonding each piezoelectric element 254a, 254b the to the ultrasonic waveguide 252 for the ground connection using solder, conductive epoxy, or other techniques described herein. Compression can be used to maintain electrical contact to the acoustic train without making a permanent connection. This can cause an increase in device thickness and should be controlled to avoid damaging the piezoelectric elements 254a, 254b. Low compression can damage the piezoelectric element 254a, 254b by a spark gap and high compression can damage the piezoelectric elements 254a, 254b by local mechanical wear. In other techniques, metallic spring contacts may be employed to create electrical contact with the piezoelectric elements 254a, 254b. Other techniques may include foil-over-foam gaskets, conductive foam, solder. Electrical connection to both sides of the piezoelectric elements 254a, 254b the D31 acoustic train configuration. The electrical ground connection can be made to the metal ultrasonic waveguide 252, which is electrically conductive, if there is electrical contact between the piezoelectric elements 254*a*, 254*b* and the ultrasonic waveguide 252.

In various aspects, as described below, an ultrasonic medical device may comprise a transducer configured to produce longitudinal vibrations, and a surgical instrument having a transducer mounting portion operably coupled to the transducer, an end effector, and wave guide therebetween. In certain aspects, as also described below, the transducer can produce vibrations which can be transmitted to the end effector, wherein the vibrations can drive the transducer mounting portion, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer mounting portion, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

In conventional D33 ultrasonic transducer architectures as shown in FIG. 1, a bolt provides compression that acoustically couples the piezoelectric elements rings to the ultrasonic waveguide. The D31 architecture 250 according to one aspect of the present disclosure employs a variety of different techniques to acoustically couple the piezoelectric elements 254*a*, 254*b* to the ultrasonic waveguide 252. These techniques are disclosed hereinbelow.

FIG. 4A illustrates an aspect of an ultrasonic medical device 300 that incorporates one or more piezoelectric transducers 312*a,b* configured to operate in a D31 mode. The ultrasonic medical device 300 may include a surgical tool 301 having a waveguide 310 and a transducer mounting portion 320 (e.g., a transducer base plate). In some aspects, the surgical tool 301 may be fabricated from sheet stock and have essentially flat faces 325 and side edges 327 orthogonal to the flat faces 325. The waveguide 310 may include an end effector at a distal end and a longitudinal portion connecting the end effector with the transducer mounting portion 320 (located at a proximal end of the surgical tool 301). One or more piezoelectric transducers 312*a,b* may be affixed to the transducer mounting portion 320 of the surgical tool 301. In certain aspects, the waveguide 310 may also include one or more stabilizing silicone rings or compliant supports 306 positioned at, or at least near, a plurality of vibration nodes, which may dampen undesirable vibration and isolate the ultrasonic energy from a sheath at least partially surrounding the surgical tool 301. In order for the piezoelectric transducers 312*a,b* to operate in a D31 mode, a first electrode may be electrically coupled to an exposed face of a transducer (for example 312*a*) that is opposite to the face of the transducer in mechanical communication with a face 325 of the surgical tool 301. In some aspects, a conductive electrode (for example, a silver electrode) may be painted or screen printed on an exposed face of the piezoelectric transducers 312*a,b* and conducting wires may then be soldered onto the conductive electrodes. Alternatively, the wires may be affixed to the exposed faces of the piezoelectric transducers 312*a,b* by means of a conductive epoxy. The surgical tool may be electrically coupled to a second electrode, thereby permitting an electric field to be imposed on the piezoelectric transducer orthogonal to a longitudinal axis of the surgical tool 301.

FIG. 4B is a close-up view of the transducer mounting portion 320 of the ultrasonic medical device of FIG. 4A, illustrating the mechanical contacts that may be made between a face of each of the piezoelectric transducers 312*a,b* and a face 325 of the surgical tool 301. In the aspect illustrated in FIG. 4B, a single pair of piezoelectric transducers 312*a,b* contact the surgical tool 301 based on a face of each transducer 312*a,b* contacting an opposing face of the surgical tool. It may be observed that each of the pair of piezoelectric transducers 312*a,b* is positioned opposite the other. As disclosed above with respect to FIG. 1, the piezoelectric transducers 312*a,b* may be activated by a power source at a predetermined frequency to induce a standing mechanical wave along the body of the surgical tool 301. The standing wave may be proportional to the predetermined frequency component of the electrical signal. The standing wave induced along the body of the surgical tool 301 may be characterized by one or more nodes and anti-nodes. The standing wave nodes may be effectively centered at one or more node locations on the surgical tool 301, and the standing wave anti-nodes may be effectively centered at one or more anti-node locations on the surgical tool 301. Each piezoelectric transducer 312*a,b* may be symmetrically disposed about a node location in the transducer mounting portion 320 of the surgical tool 301. Such a disposition may result in each transducer 312*a*, *b* contacting a portion of the surgical tool 301 at a location having minimal mechanical displacement during the activation of the transducers 312*a,b*.

FIG. 5 illustrates a mechanism for attaching a piezoelectric transducer to the transducer mounting portion 320 of a surgical tool. A node location 510 of the surgical tool at the transducer mounting portion 320 may be identified based on the wavelength of the standing wave induced in the surgical tool. An electrically conductive adhesive 520 may be applied to the face 325 of the transducer mounting portion 320 centered around the node location 510 of the surgical tool. Additionally, a high strength adhesive 530 may be applied to the face 325 of the transducer mounting portion 320 near the electrically conductive adhesive 520 and somewhat distant from the node location 510. In some aspects, the electrically conductive adhesive 520 may include an electrically conductive epoxy adhesive. In some aspects, the high strength adhesive 530 may include a high strength epoxy adhesive. As disclosed above, the piezoelectric transducers may operate in a D31 mode if the activating electric field is oriented orthogonal to the axis of the surgical tool. Thus, a first electrode may contact the piezoelectric transducer on one face opposing the face of the transducer in contact with the surgical tool. The surgical tool may form the second electrode. The electrically conductive adhesive 520 may thus provide the piezoelectric transducer with an electrical contact with the surgical tool, while the high strength adhesive 530 may form a mechanically stable contact between the piezoelectric transducer and the surgical tool.

FIGS. 6-9 depict alternative aspects of an ultrasonic medical device including multiple pairs of piezoelectric transducers. FIG. 6 illustrates the transducer mounting portion 320 of a surgical tool having a first pair of piezoelectric transducers 312*a,b* contacting the surgical tool and each of a second pair of piezoelectric transducers 612*a,b* may contact an exposed face of one of the first pair of transducer 312a,b. The second pair of piezoelectric transducers 612a,b may have the same or smaller dimensions as the first pair 312a,b.

FIG. 7 depicts a total of four piezoelectric transducers 712a-d disposed as a pair of transducers 712a,b contacting a first face of the transducer mounting portion 320 of the surgical tool and a second pair of transducer 712c,d disposed opposite to the first pair of transducers 712a,b and contacting an opposing face of the surgical tool. In some aspects, piezoelectric transducers 712a and 712c may be disposed on one side of a node location of the transducer mounting portion 320, while piezoelectric transducers 712b and 712d may be disposed adjacent to piezoelectric transducers 712a and 712c, respectively, and on a second side of the node location.

In another aspect, illustrated in FIG. 8, a total of four piezoelectric transducers 812a-d disposed as a pair of transducers 812a,b contacting a first face of the transducer mounting portion 320 of the surgical tool and a second pair of transducer 812c,d disposed opposite to the first pair of transducers 812a,b and contacting an opposing face of the surgical tool. In some aspects, piezoelectric transducers 812a and 812c may be disposed at some distance from a node location of the transducer mounting portion 320, while piezoelectric transducers 812b and 812d may be disposed symmetrically about the node location with respect to piezoelectric transducers 812a and 812c and at the same distance from the node location. Alternatively, piezoelectric transducers 812a and 812c may be centered about a first node location of the transducer mounting portion 320, while piezoelectric transducers 812b and 812d may be centered about a second node location.

FIG. 9 illustrates an aspect in which a first transducer 912a comprises a first planar array of first transducer plates and the second transducer 912b comprises a second planar array of second transducer plates. As illustrated in FIG. 9, the first transducer 912a comprises a first planar array of first transducer plates indicated by numbers 1, 2, 3, and 4. The second transducer 912b comprises a second planar array of second transducer plates (not visible in the perspective view of FIG. 9) indicated by numbers in parentheses (5), (6), (7), and (8). It may be understood that second transducer plate (5) is disposed on an opposing side of the transducer mounting portion 320 with respect to first transducer plate 1, second transducer plate (6) is disposed on an opposing side of the transducer mounting portion 320 with respect to first transducer plate 2, second transducer plate (7) is disposed on an opposing side of the transducer mounting portion 320 with respect to first transducer plate 3, and second transducer plate (8) is disposed on an opposing side of the transducer mounting portion 320 with respect to first transducer plate 4. Transducer plates 1, (5), 3, and (7) may be disposed about one side of a node location and transducer plates 2, (6), 4, and (8) may be disposed about an opposing side of the node location.

It may be understood that the transducers or transducer plates depicted in the aspects in FIGS. 1, 3-4, 6-9 may all be made of the same material. Alternatively, the transducers or transducer plates depicted in the aspects in FIGS. 1, 3-4, 6-9 may be made of different materials. For example the transducers or transducer plates may be fabricated from piezoelectric materials that differ in their respective strain constants, dielectric dissipation or dampening properties, dielectric constants, voltage sensitivities, or Currie temperatures. Similarly, the transducers or transducer plates may all have the same shape and size. Alternatively, transducers or transducer plates may differ in shape, size, or both shape and size depending on their respective placements on the surgical tool or on each other.

Each transducer or transducer plate illustrated in FIGS. 1, 3-4, 6-9 may be individually activated. In some aspects, each transducer or transducer plate may be activated by a separate ultrasonic signal generator in which the individual ultrasonic signal generators have a common ground in electrical communication with the surgical tool. In such an aspect, each transducer or transducer plate may be activated by a separate electric signal. In some examples, the electrical characteristics of the separate electrical signals may be the same, for example having the same amplitude, frequency, and phase. In alternative examples, the electrical characteristics of the separate electrical signals may differ in one or more of amplitude, frequency, and phase. In alternative aspects, each transducer or transducer plate may be activated by the same ultrasonic signal generator, but may be separately activatable by one or more transducer activation switches. Such switches may direct a first polarity of an ultrasonic signal to one set of transducers or transducer plates and a second polarity of the ultrasonic signal to a second set of transducers or transducer plates. It may be understood that such switches may also be used to disconnect one or more transducers or transducer plates from the ultrasonic signal generator while allowing other transducers or transducer plates to receive an ultrasonic signal from the ultrasonic signal generator.

In at least one such aspect, the surgical instrument can comprise a handle which can comprise one or more switches which can be configured to selectively actuate the transducers or transducer plates. For example, a switch can be moved from an off position to a first position in order to actuate a first transducer or set of transducer plates, to a second position to actuate the second transducer or set of transducer plates. It may be recognized that in an aspect such as depicted in FIG. 9, such a switch may have multiple positions, each position configured to actuate a specified group of transducer plates. In certain other aspects, a handle can comprise a first switch configured to selectively actuate a first transducer or set of transducer plates, and, in addition, a second switch configured to selectively actuate the second transducer or set of transducer plates. In such aspects, the surgeon can select the power to be supplied to the surgical tool and/or end effector.

It may be recognized that switched activation of the transducers or transducer plates may result in vibrational patterns of the surgical tool that are more complex than a single longitudinal standing mechanical wave. Such complex mechanical waves may be used to impart complex movement to the end effector of the surgical tool. For example, with respect to the aspect illustrated in FIG. 9, a predominantly transverse flapping motion may be induced in the end effector if transducer plates 1, 2, (5), and (6) are activated with a first polarity ultrasonic signal while transducer plates 3, 4, (7), and (8) are activated with a second and opposing polarity ultrasonic signal. A predominantly transverse hooking motion may be induced in the end effector if transducer plates 1, (5), 3, and (7) are activated with a first polarity ultrasonic signal while transducer plates 2, (6), 4, and (8) are activated with a second and opposing polarity ultrasonic signal. A predominantly torsional motion may be induced in the end effector if transducer plates 1, (7), 2, and (8) are activated with a first polarity ultrasonic signal while transducer plates 3, (5), 4, and (6) are activated with a second and opposing polarity ultrasonic signal. A combination of torsional and transverse motions may be induced in the end effector if transducer plates 1, (7), 4, and (6) are activated with a first polarity ultrasonic signal while transducer plates (5), 3, 2, and (8) are activated with a second and opposing polarity ultrasonic signal. Additional motions may be achieved through the activation of other groups of transducer plates.

Figure 10:
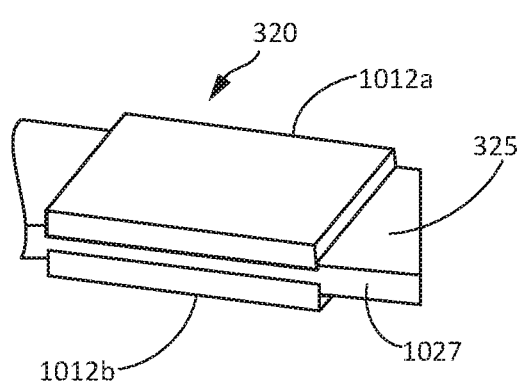
FIGS. 10 and 11 are perspective views of a transducer mounting portion of an ultrasonic medical device having a pair of piezoelectric transducers imbedded in a surgical tool, according to one aspect of this disclosure.
Figure 11:
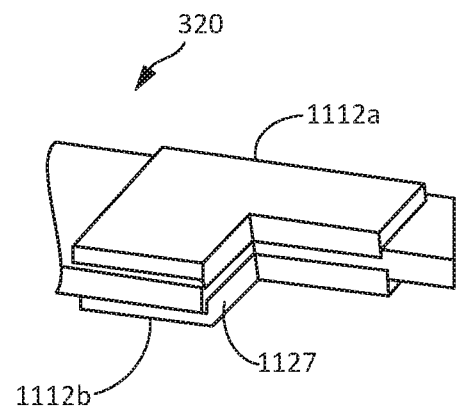

FIGS. 10 and 11 illustrate additional mechanisms by which the transducers may be affixed onto the surgical tool. The piezoelectric transducers may be mounted on the transducer mounting portion 320 of a surgical tool. The face 325 of the surgical tool may be machined to form a pocket in which the piezoelectric transducers may be mounted. As illustrated in FIG. 10, the piezoelectric transducers 1012a,b may have a width approximately equal to the width of the surgical tool, so the pocket may be fabricated across the width of the surgical tool and may extend to the edges 1027 of the surgical tool. As illustrated in FIG. 11, the piezoelectric transducers 1112a,b may have a width less than the width of the surgical tool, so the pocket may be fabricated within the width of the surgical tool but may not extent to the edges 1127 of the surgical tool. As illustrated in FIGS. 10 and 11, the thickness of the surgical tool within the pocket may be less than the overall thickness of the surgical tool. The piezoelectric transducers (1012a,b in FIGS. 10 and 1112a,b in FIG. 11) may be fixed within the respective pockets through the use of one or more adhesives, such as electrically conductive adhesives and/or high strength adhesives. Alternatively, the piezoelectric transducers (1012a,b in FIGS. 10 and 1112a,b in FIG. 11) may be fixed within the respective pockets by means of an interference fit. The interference fits may be accomplished by heating and cooling the surgical tool, thereby causing thermal expansion and contraction of the pocket of the surgical tool. The interference fits may also be accomplished by activating and deactivating the piezoelectric transducers, thereby causing piezoelectric expansion and contraction of the piezoelectric transducers.

Figure 12:
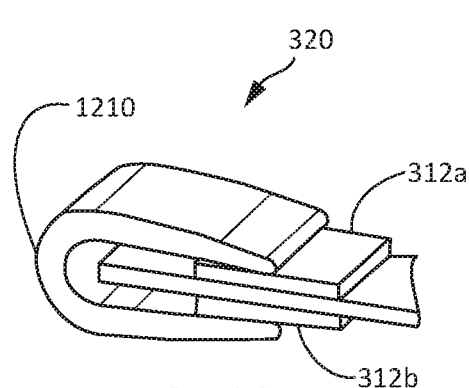
FIGS. 12 and 13 are perspective views of a transducer mounting portion of an ultrasonic medical device having a pair of piezoelectric transducers held by one or more securing clips, according to one aspect of this disclosure.
Figure 13:
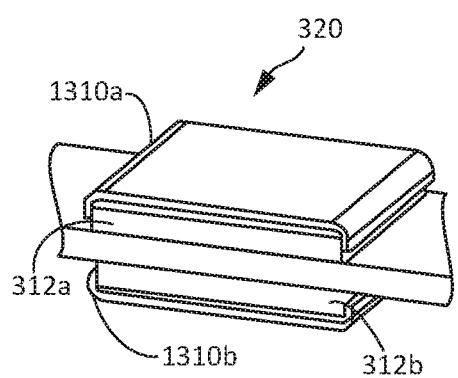

FIGS. 12 and 13 illustrate further mechanisms by which the transducers may be affixed onto the surgical tool by the use of one or more clips. FIG. 12 illustrates the use of a single clip 1210, such as a C-clip that may compress each of the piezoelectric transducers 312a,b against their respective faces of the transducer mounting portion 320 of the surgical tool. FIG. 13 depicts clips 1310a,b that may be used to apply a pre-loading compression across a longitudinal direction of the piezoelectric transducers 312a,b. The piezoelectric transducers 312a,b illustrated in FIG. 13 may be affixed to the surgical tool through one or more adhesives as disclosed above (for example in FIG. 5).

Figure 14:
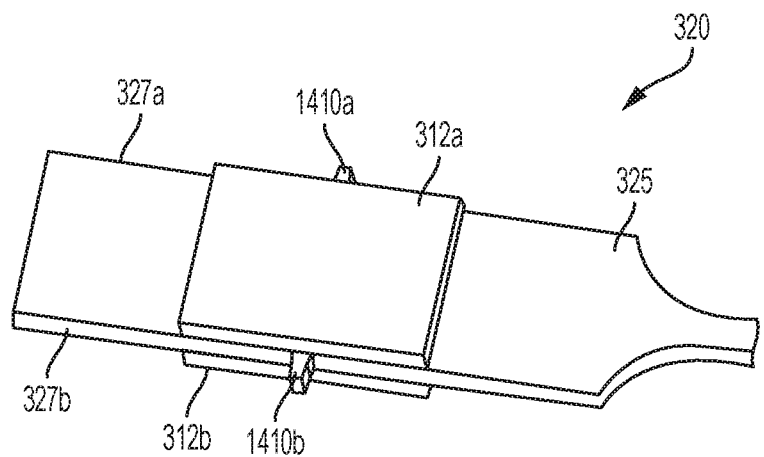
FIG. 14 is a perspective view of a transducer mounting portion of an ultrasonic medical device including mounting flanges, according to one aspect of this disclosure.

The ultrasonic medical device depicted in FIG. 3 may also incorporate features for mounting in an ultrasound system. FIG. 14 illustrates an aspect of an ultrasonic medical device adapted for mounting in a housing. As depicted in FIG. 14, the ultrasonic medical device may include a surgical tool having a transducer mounting portion 320 comprising faces (such as face 325) and edges such as edge 327). Piezoelectric transducers 312a,b may be mounted on the transducer mounting portion 320 and disposed symmetrically about a node location in the surgical tool. The surgical tool may be fabricated to incorporate flanges 1410a,b located at the node location on opposing edges 327a,b of the surgical tool. As depicted in FIG. 14, the first flange (for example 1410a) may extend from a first side edge 327a of the surgical tool and the second flange (for example 1410b) may extend from an opposing side edge 327b of the surgical tool, so that each of the first flange 1410a and the second flange 1410b may be symmetrically disposed about the node location in the surgical tool.

In various aspects, further to the above, an ultrasonic medical device may comprise a surgical tool comprising a transducer mounting portion, a waveguide, and an end effector, along with one or more piezoelectric transducers affixed thereon. The ultrasonic medical device may further comprise a housing at least partially surrounding the transducer mounting portion of the surgical tool and a sheath at least partially surrounding the waveguide and/or end effector. In at least one aspect, an ultrasonic medical device can comprise one or more piezoelectric transducers, a housing encompassing transducer mounting portion, waveguide, a sheath encompassing the waveguide, and an end effector. In certain aspects, the ultrasonic medical device can further comprise one or more stabilizing supports which can be configured to support the waveguide and/or end effector within the sheath. In at least one such aspect, the sheath can comprise a handle portion and/or can be configured to be grasped, or gripped, by a surgeon such that the surgeon can accurately manipulate the ultrasonic medical device and, in particular, accurately manipulate a distal end of the end effector. In at least one aspect, at least a portion of the outer surface of the sheath can comprise a roughened and/or textured surface. In certain aspects, the outer surface of the sheath can comprise a round, or at least substantially round, cross-section having a diameter of approximately 5 millimeters, approximately 10 millimeters, approximately 15 millimeters, and/or a diameter between approximately 4 millimeters and approximately 16 millimeters.

Figure 15:
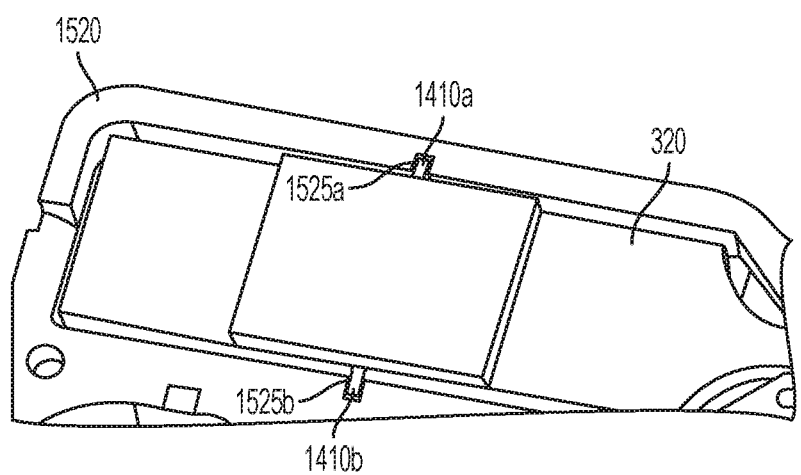
FIG. 15 is a perspective view of a transducer mounting portion of the ultrasonic medical device of FIG. 14 mounted in a housing, according to one aspect of this disclosure.
Figure 16:
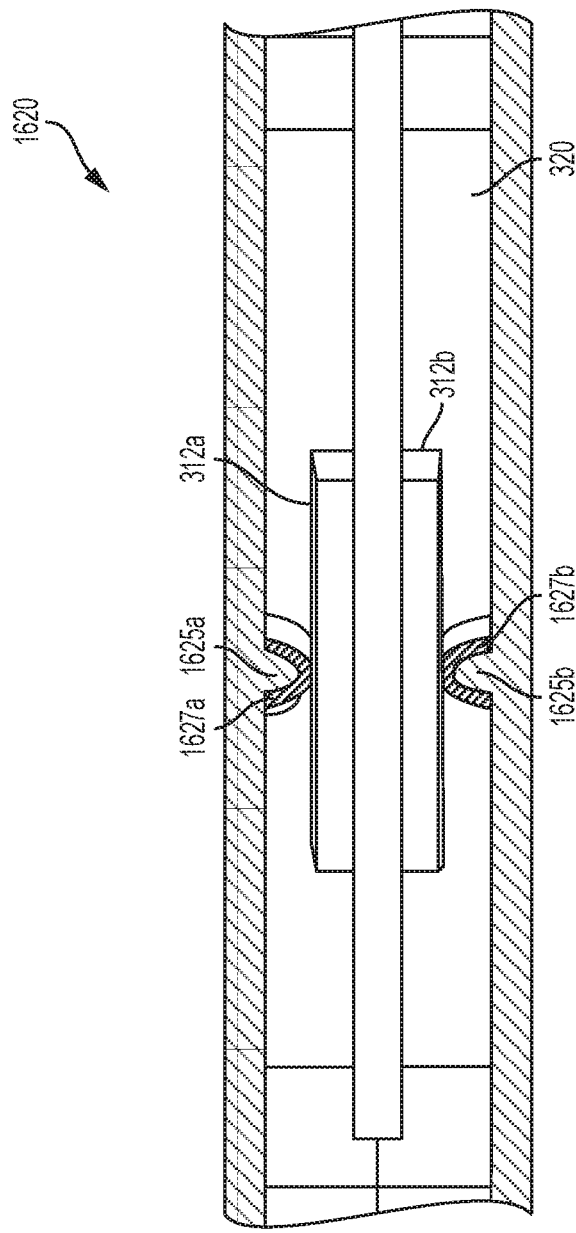
FIG. 16 is a side view the transducer mounting portion of the ultrasonic medical device of FIG. 1 mounted in a housing, according to one aspect of this disclosure, according to one aspect of this disclosure.

The ultrasonic medical device of FIG. 14 may be mounted in a housing as depicted in FIG. 15. The transducer mounting portion 320 may be mounted within a housing 1520 that includes retainers 1525a,b, in which each retainer 1525a,b is configured to receive one of the flanges 1410a,b. Such an arrangement may allow the surgical tool to move according to the standing wave induced therein, while being held securely in the housing 1520 at a node point that generally does not move while the piezoelectric transducers are activated. FIG. 16 illustrates an additional aspect for securing an ultrasonic medical device within a housing. FIG. 16 depicts the transducer mounting portion 320 of a surgical tool having a pair of piezoelectric transducers 312a,b mounted thereon. The housing may include a shroud 1620 that may surround the surgical tool. The shroud 1620 may include one or more contacts 1625a,b configured to apply a compressive force to the piezoelectric transducers 312a,b. The contacts 1625a,b may be designed to apply the compressive force to the piezoelectric transducers 312a,b approximately at a node location of the surgical tool when the piezoelectric transducers 312a,b are activated by an ultrasound generator. The contacts 1625a,b may be electrically conductive to permit power from the ultrasound generator to activate the piezoelectric transducers 312a,b. Alternatively, the contacts 1625a,b may include electrically conducting surfaces 1627a,b that directly contact the exposed surfaces of the piezoelectric transducers 312a,b. The electrically conducting surfaces 1627a,b that may be placed in electrical communication with the ultrasound generator to conduct energy from the ultrasound generator to the piezoelectric transducers 312a,b. Aspects of the ultrasonic medical device, as disclosed above, incorporate a surgical tool generally described as being manufactured from flat stock. However, additional aspects may include a surgical tool that may be manufactured from round stock or square stock (such as a long bar). FIGS. 17 and 18 depict aspects of an ultrasonic medical device manufactured from either round or square stock. Such an ultrasonic medical device may have a waveguide 1710 having a cylindrical or truncated conical cross section and a transducer mounting portion 1720 having a square or rectangular cross section. Alternatively, the waveguide 1710 may have the form of a double wedge with appropriate tips to achieve desired tissue effect. Double-wedge horns are well known in ultrasonic welding.

The transducer mounting portion 1720 of such an ultrasonic device may be described as having the form of a square or rectangular prism. While a surgical tool manufactured from flat stock may have a single pair of surfaces (see 325 of FIG. 3) on which the piezoelectric transducers may be mounted, a surgical tool having a transducer mounting portion 1720 having the form of a square or rectangular prism may have four surfaces on which the piezoelectric transducers 1712a-c may be mounted (note that a fourth piezoelectric transducer, in addition to the three piezoelectric transducers 1712a-c illustrated in FIG. 17, may be affixed to a fourth side of the transducer mounting portion 1720 that is not shown in the view). The multiple piezoelectric transducers may be affixed to the surfaces of the transducer mounting portion 1720 using adhesives as disclosed above with respect to FIG. 5. Alternatively, a clip or band 1810 may be used to secure the multiple piezoelectric transducers. It may be understood that the clip or band 1810 may be designed to incorporate electrodes to supply an electrical signal to activate the multiple piezoelectric transducers.

FIGS. 17 and 18 depict a surgical tool with a transducer mounting portion 1720 having the form of a square or rectangular prism on which each of the piezoelectric transducers 1712a-c (including the transducer not depicted in the figures) may be mounted. It may be recognized that a piezoelectric transducer may be mounted on each of the four sides of the transducer mounting portion 1720 or only on a pair of opposing sides. Further, each of the piezoelectric transducers 1712a-c may comprise one or more transducer plates (similar in structure as depicted in FIG. 9). In some examples, the width of piezoelectric transducers 1712a-c may be half that of the piezoelectric transducers 312a,b (see FIG. 3) that may be used on surgical tools fabricated from flat stock to preserve the total volume. In some fabricated examples, a piezoelectric transducer, such as 1712a, was able to deliver 35 watts.

As disclosed above with respect to FIGS. 7-9, each of the piezoelectric transducers 1712a-c (including the hidden fourth transducer) may be activated by the same or different power supplied. If all four transducers are driven in parallel, the motion of the end effector of the surgical tool may be longitudinal (similar to the motion of a flat ultrasonic medical device comprising a surgical tool fabricated from sheet stock, as depicted in FIG. 3). However, if two transducers, located on opposing faces of the transducer mounting portion 1720 are driven out of phase, then a transverse motion may be produced in the end effector. If the two transducers on the other faces are driven out phase, then a transverse motion of the end effector may be produced in the opposite direction. Further, if each of a first pair of opposing transducers is driven at 180 degrees apart, and each of a second pair of opposing transducers is driven at 180 degrees apart and further are driven 90 degrees apart from the first pair, then an orbital motions may be produced at the end effector. It may be recognized that the geometry of the waveguide 1710 and driving frequency of the transducers may be designed to achieve a longitudinal, transverse, and orbital motion in one device.

Aspects depicted in FIGS. 17 and 18 may benefit from low-cost fabrication methods to produce a square/rectangular transducer with a relatively small cross section. As disclosed above, the use of independent activation signals to the transducers having appropriate driving characteristics in frequency and phase, may result in longitudinal, transverse (in two directions) and orbital motions. Such an orbital motion with a hollow blade may provide improved fragmentation and skeltonization of tissue. Additionally, such multiple controllable motions may form the basis for dynamic steering of an end effector, which may include a light source or sensor.

Figure 20:
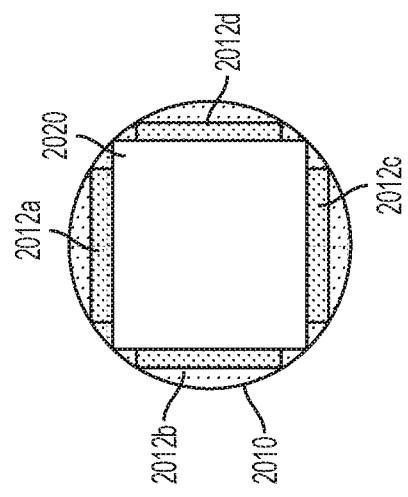
FIG. 20 is a cross-sectional view of an ultrasonic medical device fabricated from round stock, according to one aspect of this disclosure.
Figure 19:
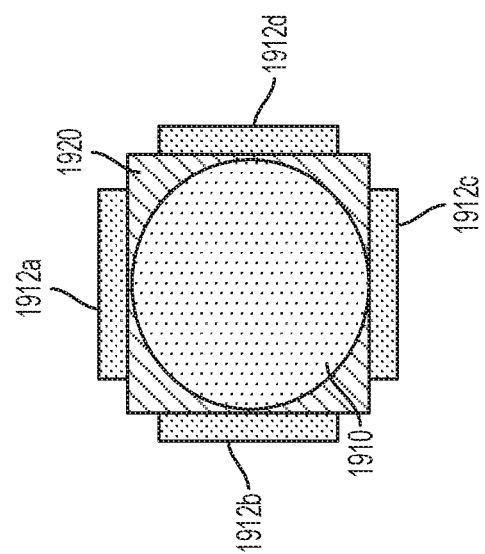
FIG. 19 is a cross-sectional view of an ultrasonic medical device fabricated from square stock, according to one aspect of this disclosure.

FIGS. 19 and 20 depict a cross section of an ultrasonic medical device manufactured from bar stock and round stock, respectively. FIG. 19 illustrates a medical device having a cylindrical waveguide 1910 machined from a bar stock, for example on a lathe. The un-machined portion, having a square cross-section, is retained at the transducer mounting portion 1920 of the medical device. A piezoelectric transducer (1912a-d) may be mounted on each surface of the transducer mounting portion 1920 of the device. FIG. 20 illustrates a medical device, comprising a transducer mounting portion 2020 having a square cross section, machined from round stock, for example by a milling machine. The un-machined portion, having a circular cross-section, is retained for the waveguide 2010. A piezoelectric transducer (2012a-d) may be mounted on each surface of the transducer mounting portion 2020 of the device.

Figure 21:
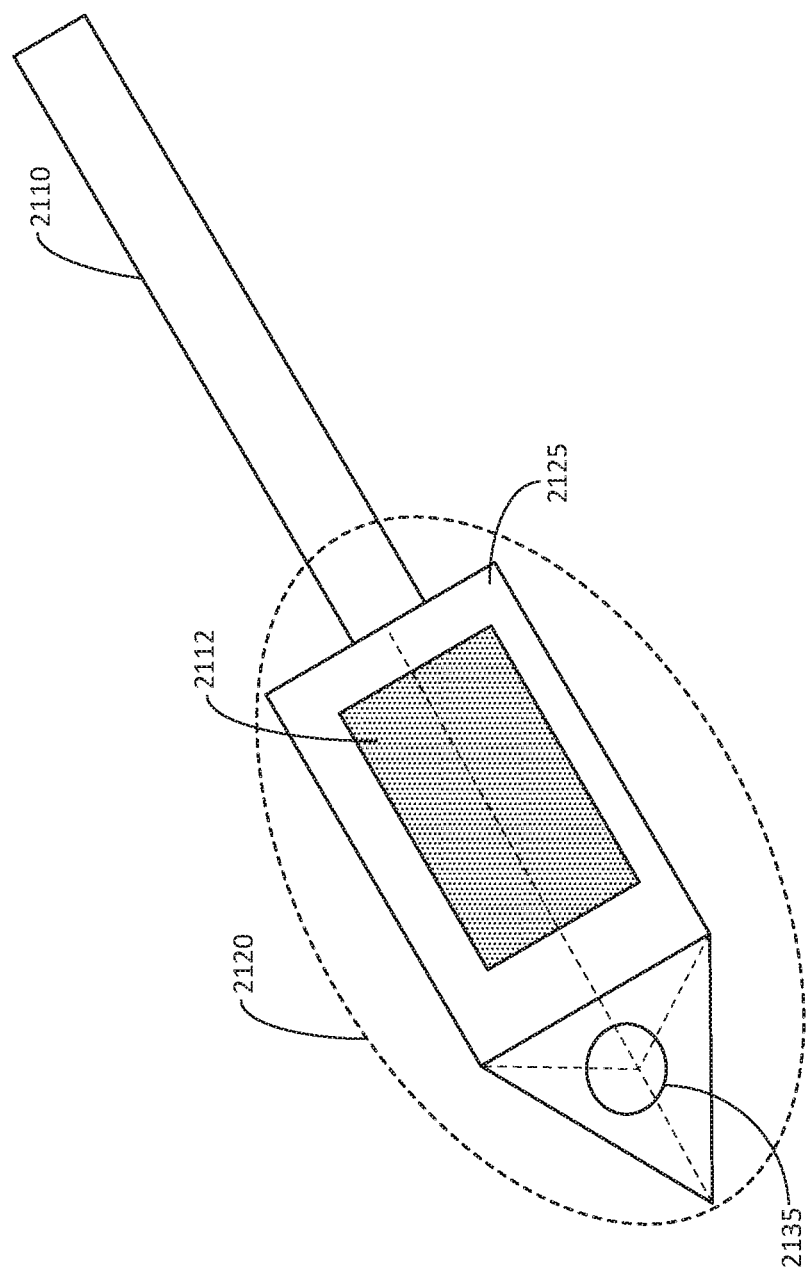
FIG. 21 is a perspective view of an ultrasonic medical device having a transducer mounting portion having a form of a triangular prism, according to one aspect of this disclosure.

FIG. 21 depicts another aspect of an ultrasonic medical device having a transducer mounting portion 2120 fabricated in the form of a triangular prism. Such a medical device may also include a waveguide 2110 having a round, flat, square, or other cross section as disclosed above. In one aspect, a piezoelectric transducer 2112 may be affixed to each of the faces (such as face 2125, as illustrated in FIG. 21). As disclosed above with respect to aspects having more than two transducers, each transducer may be activated from a common power supply or from individual power supplies. The transducers may also be activated in phase or out of phase. In one example, if all three transducers are driven in parallel, the motion of the end effector may be primarily longitudinal. In another example, in an aspect having a transducer mounting portion 2120 fabricated in the form of a triangular prism, the transducers may be activated 120 degrees apart from each other. Such an activation may result in a rotational or torsional motion at the end effector. If two of the transducers are driven with a greater amplitude than the third (including not driving the third at all), then a mainly lateral motion may be induced in the end effector.

Additionally, each of the transducers may be operated at a different frequency, which may result in more complex motions of the end effector. In another example, the current delivered to each transducer may be modulated so that one or two transducers may be activated with the other(s) off (inactivated for a period of time, and then one or two other transducers may be activated (with the first one or two transducers remaining in an off or inactivated state) after a brief rest period. The rest period may be long enough for transients to die down and drive at resonance for some time. For example, the rest period may be between about 0.1 and 1 msec. The use of such a rest period between successive activations of the transducers may be useful for "soft" start-ups and shut downs. As disclosed above with respect to FIG. 17, it may be recognized that the geometry of the waveguide 2110 and driving frequency of the transducers may be designed to achieve a longitudinal, transverse, and orbital motion in one device. It may be recognized that one-phase to three-phase converters are well known in industrial electrical systems to power motors, for example. It may also be possible to have a small converter on a circuit board that is contained in the transducer body. The 120 phase difference between the transducers may be achieved with lead- and lag-circuits from passive components.

The ultrasonic medical device depicted in FIG. 21 may be fabricated from a surgical tool having a triangular prismatic transducer mounting portion 2120. A piezoelectric transducer, such as transducer 2112, may be affixed to each of the faces 2125 of the surgical tool. In an alternative aspect, the ultrasonic medical device may lack a triangular prismatic transducer mounting portion 2120, but rather incorporate three piezoelectric transducers attached directly to each other along their neighboring length-wise edges. The waveguide 2110 may terminate at a proximal end with a triangular frame or plate to which the three piezoelectric transducers may be affixed at their respective distal edges.

Additionally, the ultrasonic medical device may include a lumen 2135 disposed within the device and fabricated along a central longitudinal axis thereof. The lumen 2135 may be used to transport a fluid, such as a cooling fluid, through the device. If the lumen 2135 extends throughout the entire length of the device, having a distal portal at a distal end of the end effector, the cooling fluid may be used to cool tissue contacting the end effector. Alternatively, the lumen 2135 may be in fluid communication with a proximal vacuum source that may be used to remove fluids from the tissue at the distal end of the end effector.

Figure 25:
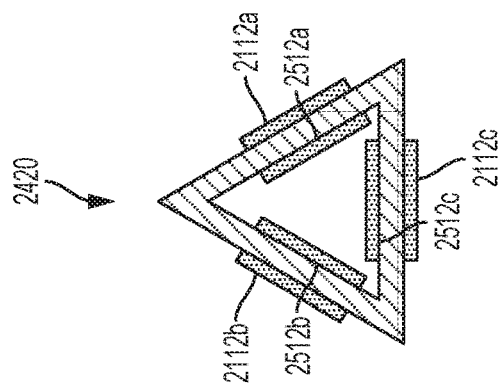
FIGS. 22-25 are cross-sectional views of a transducer mounting portion of an ultrasonic medical device in which the transducer mounting portion has a form of a triangular prism, according to one aspect of this disclosure.
Figure 24:
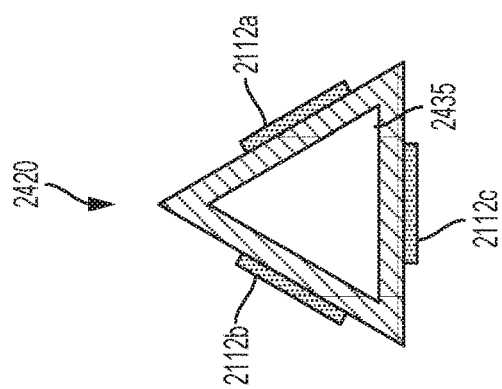
Figure 23:
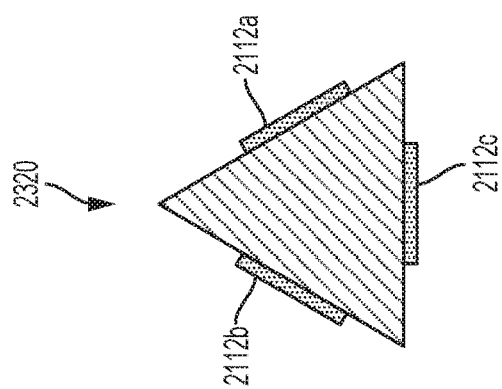
Figure 22:
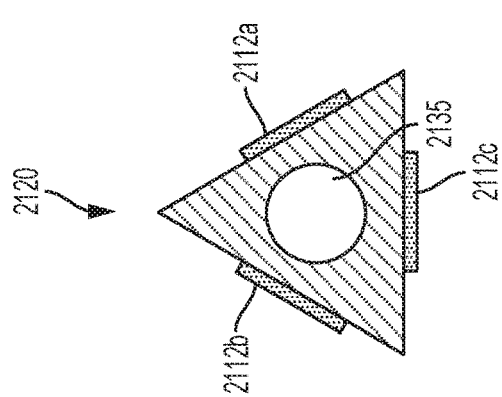

FIGS. 22-25 depict a variety of aspects of an ultrasonic medical device having a triangular prismatic transducer mounting portion. FIG. 22, for example, is a cross-sectional view of the ultrasonic medical device illustrated in FIG. 21. It may be observed that the transducer mounting portion 2120 has a piezoelectric transducer 2112a-c affixed to each of the faces of the transducer mounting portion 2120, and a central, cylindrical lumen 2135 disposed therein. FIG. 23, for example, is a cross-sectional view of the ultrasonic medical device having a transducer mounting portion 2320 that lacks a central lumen. FIG. 24, for example, is a cross-sectional view of the ultrasonic medical device having a hollow triangular prismatic transducer mounting portion 2420 that has a triangular lumen 2435. FIG. 25, for example, is a cross-sectional view of the ultrasonic medical device of FIG. 24, having a hollow triangular prismatic transducer mounting portion 2420 that has a triangular lumen 2435. FIG. 25 also illustrates that piezoelectric transducers 2512a-c may be mounted on the inner faces of the triangular lumen.

Generalizing from FIGS. 3-25, a surgical tool may include a transducer mounting portion fabricated in the form of a polygonal prism (the transducer mounting portion of the surgical tools disclosed in FIGS. 3-16 may be considered to have the form of a rectangular prism in which one set of opposing sides is much longer than the second set of opposing sides). It may be recognized that additional aspects of a surgical tool may include a transducer mounting portion having the form of a cylindrical or partially cylindrical prism.

FIGS. 26-31 are directed to aspects of an ultrasonic medical device comprising a surgical tool having a cylindrical, or partially cylindrical, transducer mounting portion. FIG. 26 illustrates an ultrasonic medical device 2600 comprising surgical tool having a cylindrical waveguide 2610 and a transducer mounting portion 2620 having the form of a horizontal cylindrical segment formed from a pair of sectional planes parallel to the long axis of the cylinder. The transducer mounting portion 2620 may further include a pair of parallel and opposing flat surfaces 2625 on which the piezoelectric transducers 312a,b may be mounted as disclosed above with respect to FIG. 5, for example.

FIG. 27 illustrates an ultrasonic medical device 2700 comprising a surgical tool having a cylindrical waveguide 2710 and a transducer mounting portion 2720 having the form of a cylindrical prism in which a pair of opposing flats 2725a,b may be fabricated to receive the piezoelectric transducers 312a,b. As disclosed with respect to FIGS. 10 and 11, the piezoelectric transducers 312a,b may be affixed to the flats 2725a,b by means of one or more types of adhesives. Alternatively, the piezoelectric transducers 312a,b may be affixed to the flats 2725a,b by means of an interference fit. The interference fits may be accomplished by heating and cooling the surgical tool, thereby causing thermal expansion and contraction of the transducer mounting portion 2720 surrounding the flats 2725a,b. The interference fits may also be accomplished by activating and deactivating the piezoelectric transducers, thereby causing piezoelectric expansion and contraction of the piezoelectric transducers.

FIG. 28 illustrates an ultrasonic medical device 2800 comprising a surgical tool having a cylindrical waveguide 2810 and a transducer mounting portion 2820 having the form of a cylindrical prism. The piezoelectric transducer 2812 may have the form of a ring or a tube. In one aspect, the surgical tool 2800 may be fabricated from a separate waveguide 2810 and a transducer mounting portion 2820. The transducer mounting portion 2820 may include a machined portion having a smaller diameter than the remaining transducer mounting portion 2820 to receive the piezoelectric transducer 2812 (see FIG. 29). An ultrasonic medical device comprising the surgical tool 2800 and the piezoelectric transducer 2812, may be assembled from the waveguide 2810, the transducer mounting portion 2820, and the piezoelectric transducer 2812. During fabrication, a flange portion of the waveguide 2810 may be secured against an edge of the piezoelectric transducer 2812, thereby applying longitudinal compression against the transducer. In one example, the waveguide 2810 may include a threaded portion that may be threaded into a mating portion of the transducer mounting portion 2820 to assemble the ultrasonic medical device.

Figure 29:
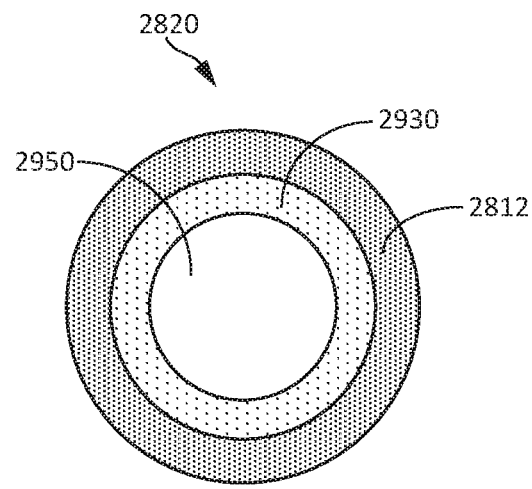
FIG. 29 is a cross-sectional view of the transducer mounting portion of the ultrasonic medical device of FIG. 28, according to one aspect of this disclosure.

FIG. 29 illustrates a cross-sectional view of the transducer mounting portion 2820 of the ultrasonic medical device depicted in FIG. 28, illustrating the piezoelectric transducer 2812 placed over smaller diameter machined portion 2950 of the transducer mounting portion 2820. It may be recognized that good conduction of the mechanical vibrations created by an energized cylindrical piezoelectric transducer 2812 into the waveguide may require tight mechanical coupling between the piezoelectric transducer 2812 and the waveguide 2810. Further, for the piezoelectric transducer 2812 to operate in a D31 mode, electrodes must form electrical contacts with the outer surface and the inner surface of the piezoelectric transducer 2812. In some aspects, an electrode connected to a hot conductor of an ultrasound power generator may contact an exposed surface of a transducer, while the surgical tool, contacting the opposing face of the transducer, may be in electrical contact with the neutral conductor of the ultrasound power supply. Because the piezoelectric transducer 2812 may be formed from a ceramic, it may be difficult to assure that the inner surface of the piezoelectric transducer 2812 forms a good electrical contact with the machined portion 2950 of the transducer mounting portion 2820. If a gap between the machined portion 2950 and the inner surface of the piezoelectric transducer 2812 is small (for example about 0.005 inches), the gap may be filled with a conductive epoxy 2930 and still deliver the needed power. Alternatively, a "green" (or un-fired) piezoelectric ceramic material may be assembled on the surgical tool and co-fired along with the surgical tool. In another alternative method of fabrication, the metallic portions of the ultrasonic medical device may be assembled with a piezoelectric ceramic that is between the green state and the fully fired state.

Figure 30:
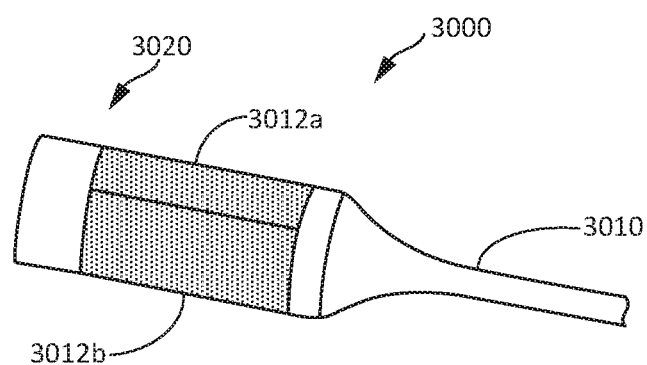
FIG. 30 is a side view of an ultrasonic medical device fabricated from round stock, according to one aspect of this disclosure.

FIG. 30 illustrates yet another aspect of an ultrasonic medical device 3000 composed of a surgical tool having a cylindrical waveguide 3010 and a cylindrical prismatic transducer mounting portion 3020. The ultrasonic medical device 3000 may be distinguished from the ultrasonic medical device 2800 in that the transducer comprises a plurality of cylindrical piezoelectric plates 3012a,b. Such cylindrical piezoelectric plates 3012a,b may be considered as being formed from longitudinal sections of a single tubular piezoelectric transducer 2812 as illustrated in FIG. 28. There may be two, three, or more cylindrical piezoelectric plates 3012; two such cylindrical piezoelectric plates 3012a,b are depicted in FIG. 30.

Figure 31:
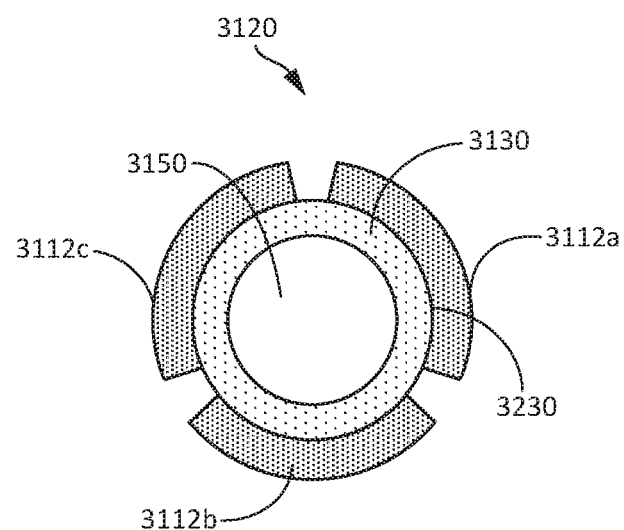
FIG. 31 is a cross-sectional view of the transducer mounting portion of the ultrasonic medical device of FIG. 30, according to one aspect of this disclosure.

FIG. 31 is a cross-sectional view 3120 of the transducer mounting portion 3020 of the ultrasonic medical device 3000 illustrated in FIG. 30. It may be recognized that the cylindrical piezoelectric plates 3012a,b depicted in FIG. 30 comprise a ceramic material that may be difficult to machine to permit a close fit, both to each other (along their respective length-wise edges) and to the machined portion 3150 of the transducer mounting portion 3120. As depicted in FIG. 31, the ultrasonic medical device (3000 of FIG. 30) may include cylindrical piezoelectric plates 3112a-c that do not contact each other along their respective length-wise edges, but may be fabricated so that their inner surfaces may conform more closely to the machined portion 3150 of the transducer mounting portion 3120. The cylindrical piezoelectric plates 3112a-c may then be affixed to the machined portion 3150 of the transducer mounting portion 3120 using a conductive epoxy 3230. As disclosed above with respect to other aspects of ultrasonic medical devices, for example the device depicted in FIG. 21, each of the individual cylindrical piezoelectric plates 3112a-c may be activated independently. For example, in the aspect depicted in FIG. 31, the three cylindrical piezoelectric plates 3112a-c may be activated by piezoelectric driving signals that are 120 degrees out of phase. Other examples of methods for activating three cylindrical piezoelectric plates 3112a-c may include those disclosed above with respect to FIG. 21. As noted above, other examples of an ultrasonic medical device 3000 may include 2, 3, 4, or more piezoelectric transducers that may be activated synchronously, asynchronously, or with a variety of ultrasound activation signals that may differ in frequency, phase, or amplitude.

Although the aspects disclosed above in FIGS. 3-31 are directed to a plurality of piezoelectric transducers positioned relative to the location of a single (for example proximal) vibrational node induced in a surgical tool, it may be recognized that transducers may similarly be positioned relative to more than one vibrational node. As disclosed above, the plurality of piezoelectric transducers may be activated by a single source of ultrasonic power or multiple sources of ultrasonic power, and may be operated synchronously or asynchronously. The electrical characteristics, such as frequency, amplitude, and phase, of the ultrasonic power may be the same or may differ among all of the plurality of piezoelectric transducers.

Figure 32:
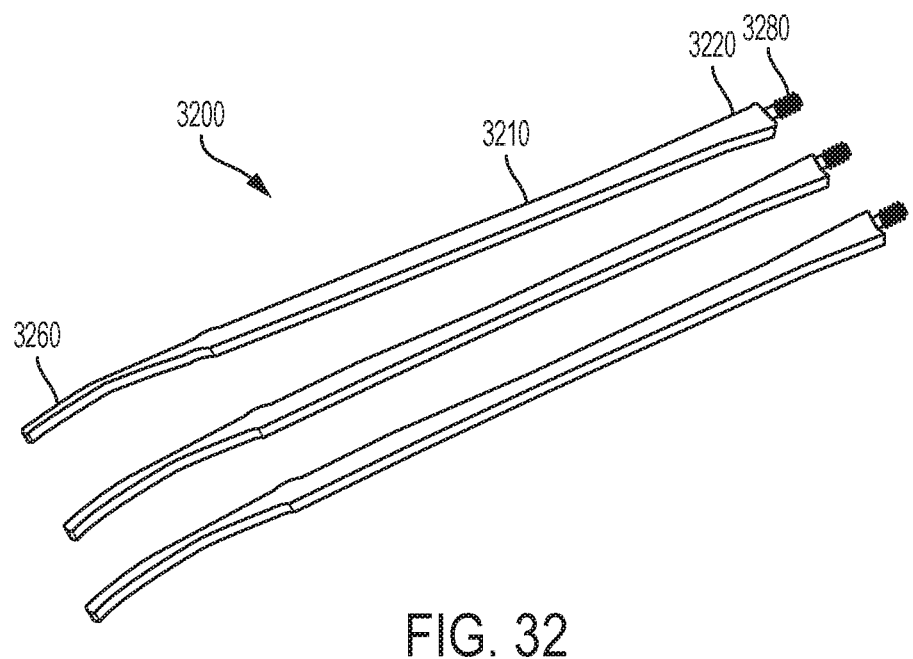
FIG. 32 is a perspective view of surgical tools for an ultrasonic medical device, according to one aspect of this disclosure.

FIG. 32 illustrates aspects of a surgical tool 3200. In some aspects, the surgical tool 3200 may be used as part of an ultrasonic system 10 as depicted in FIG. 1. Alternatively, one or more piezoelectric transducers may be mounted on the surgical tool 3200 to form an ultrasonic medical device, for example 300 as depicted in FIG. 3. The surgical tool 3200 may comprise a proximal transducer mounting portion 3220, a distal end effector 3260 and a longitudinal portion or waveguide 3210 therebetween. The surgical tool 3200 may also comprise an attachment boss 3280 that may permit the surgical tool 3200 to be mounted in a housing or other ultrasonic system. Such a surgical tool 3200 may be manufactured from titanium stock or from aluminum stock although any material having appropriate mechanical and/or electrical characteristics may be used.

Figure 33:
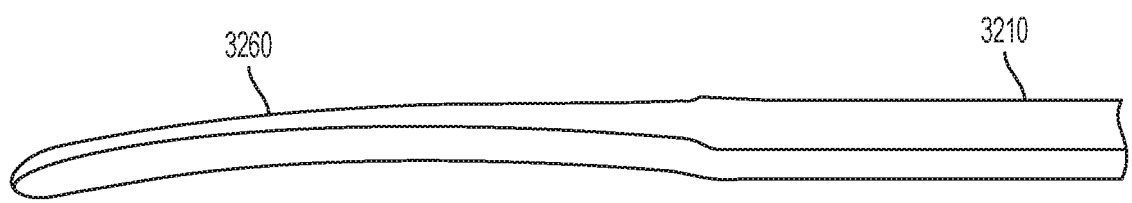
FIG. 33 is a perspective view of an end effector of a surgical tools depicted in FIG. 32, according to one aspect of this disclosure.

FIG. 33 illustrates a close-up view of the end effector 3260 and the distal end of the waveguide 3210. The waveguide 3210 may have a rectangular cross section as depicted in FIG. 33 although the cross section may of any polygon as may be appropriate for its use. Alternatively, the cross section may be elliptical or circular. The end effector 3260 may be fabricated as an integral part of the surgical tool, or may comprise a separate component affixed onto the waveguide 3210. The end effector 3260 may have a curved shape and may curve either in a vertical or horizontal direction with respect to the longitudinal axis of the surgical tool as may be appropriate for its use. Alternatively, the end effector 3260 may comprise a straight section that is bent at some angle, either vertically or horizontally, from the longitudinal axis of the surgical tool. In other examples, the end effector 3260 may comprise a more complex geometry including straight sections and curved sections, or multiple curved sections that differ in their respective radii of curvature. The end effector 3260 may extend directly from the waveguide 3210 or the waveguide 3210 may include shoulders from which the end effector 3260 extends.

In various aspects, the length and mass of a surgical tool comprising a transducer mounting portion, a wave guide, and/or an end effector can dictate the resonant frequency of the surgical tool. In various circumstances, the length of the surgical tool can be selected such that the resonant frequency of the surgical tool is within a range of frequencies that a voltage or current source can supply to a piezoelectric transducer coupled thereto. In certain aspects, a given transducer, wave guide, and/or end effector may be required to be used together and, in the event that a different length wave guide or different end effector is needed, a different surgical tool altogether may be required.

Figure 34:
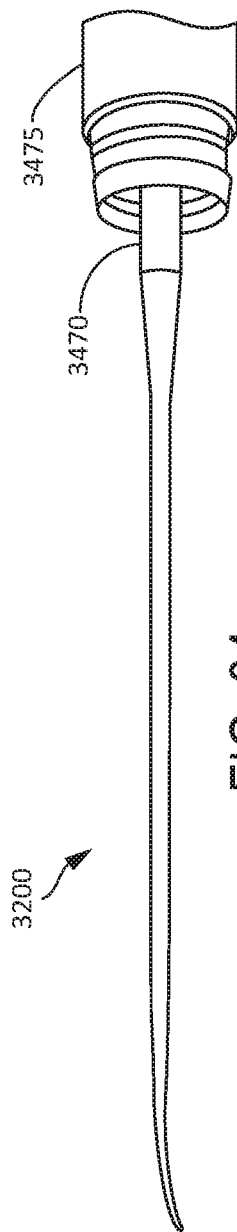
FIG. 34 is a perspective view of an ultrasonic medical device incorporating a surgical tool depicted in FIG. 32, according to one aspect of this disclosure.

FIG. 34 illustrates an example of a surgical tool 3200 mounted within an ultrasound medical system comprising a housing 3475 or a handle. The surgical tool 3200 may be secured to or within the housing 3475 according to any means consistent with its function and use. For example, the surgical tool 3200 may be secured to the housing 3475 by means of a clamp, clip, or collet 3470. For example, such an ultrasound medical system may use the surgical tool 3200 alone to contact a tissue for therapeutic means.

Figure 35:
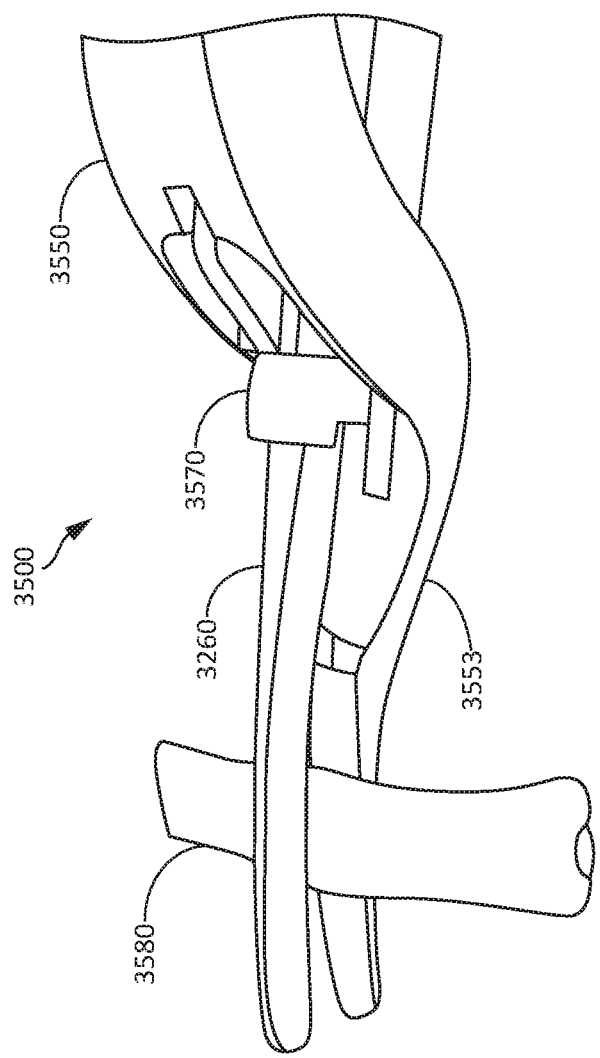
FIG. 35 is a perspective view of an ultrasonic medical device incorporating a surgical tool depicted in FIG. 32, according to one aspect of this disclosure.

FIG. 35 illustrates a more complex ultrasound medical system, such as an ultrasound shear 3500, in which a surgical tool may be incorporated. The ultrasound shear 3500 may include a surgical tool (the end effector 3260 of the surgical tool being illustrated) which may operate against an anvil 3553. The anvil 3553 may be moved by a movable handle 3550. The movable handle 3550 may be manipulated so that a tissue 3580 contacted by the anvil 3553 may be brought into contact with the end effector 3260. The surgical tool may be affixed to the ultrasound shear 3500 by means of a clamp, clip, or collet 3570.

It may be recognized that the utility of an ultrasound surgical tool is based on the standing mechanical vibrational waves that may be induced therein by an associated piezoelectric transducer. Owing to various manufacturing differences, however, each surgical tool may have a slightly different resonant frequency and, as a result, each surgical tool may be tested in order to find its resonant frequency. If it is determined that the natural frequency of the surgical tool needs to be adjusted, the transducer mounting portion of the surgical tool and/or the end effector may be ground in order to adjust their length and, as a result, adjust the resonant frequency of the surgical tool. Although such manufacturing methods may be useful for their intended purposes, the process may be time consuming and/or may not provide adequate adjustability of the surgical tool. For example, in the event that too much length is ground off of a surgical tool transducer mounting portion, for example, the surgical tool typically may be thrown out and the adjustment process must be repeated with a new surgical tool. More efficient processes for fabrication of surgical tools is therefore useful.

Figure 36:
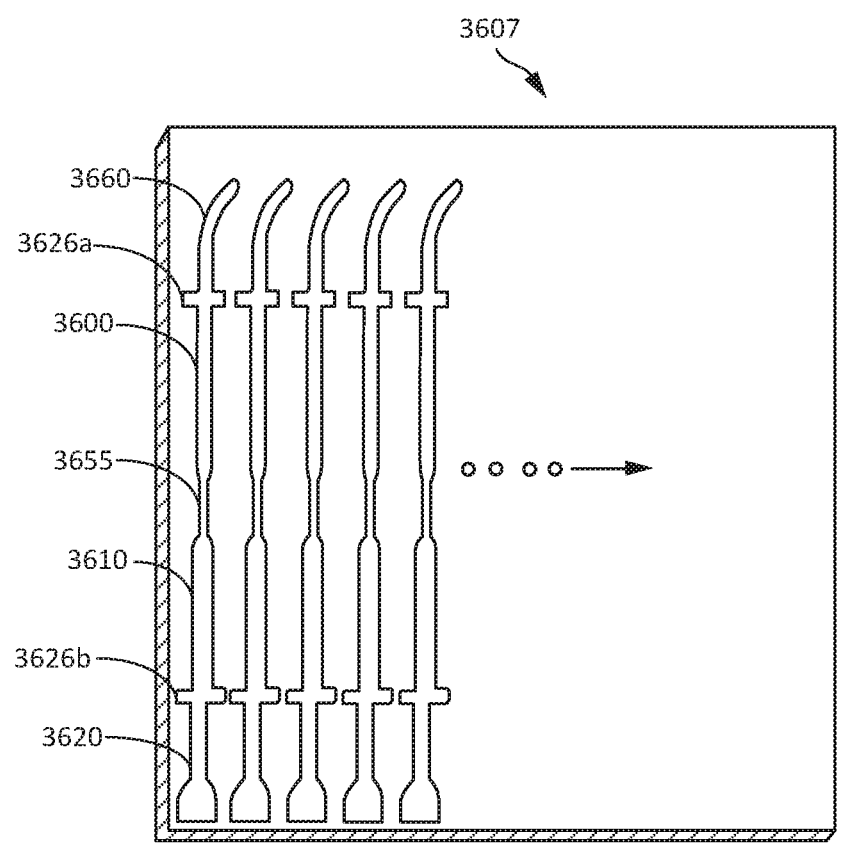
FIG. 36 is a perspective view of surgical tools during a fabrication step from flat stock, according to one aspect of this disclosure.

FIG. 36 illustrates a portion of a method of fabrication of one or more surgical tools, such as surgical tool 3600. Each surgical tool 3600 may comprise a transducer mounting portion 3620, an end effector 3660, and an elongated portion or waveguide 3610 therebetween. The surgical tool 3600 may also incorporate additional features such as a gain feature 3655 to modify the amplitude of the mechanical wave induced in the surgical tool 3600 by the activated piezoelectric transducers driving it. Additional features may include one or more blade attachment features 3626a,b that may be used for attaching the surgical tool to a housing or ultrasound medical system. In some examples, the attachment features 3626a,b may be fabricated at one or more node locations of the surgical tool 3600 where mechanical displacement during piezoelectric activation may be minimized.

The surgical tool 3600 may be fabricated from sheet stock 3607 comprising titanium or aluminum. Titanium or other surgical tool 3600 material may be rolled, pressed, molded, or cast into sheets 3607 in a manner that creates the best material microstructure and orientation (grain) to produce efficient surgical tools 3600. The surgical tools 3600 may be "blanked" by way of laser machining, laser machining with tilt degree of freedom, wire EDM, conventional milling, stamping, fine blanking, or other two dimensional cutting method from the sheet 3607. In some aspects, the surgical tools 3600 may be bulk finished to round edges by way of tumbling, sand blasting, bead blasting, electropolishing, forging, coining, or other finishing methods. In alternative aspects, only those areas or features on the surgical tool 3600 that require further shape refinement may be machined to their final dimensions. Such portions of the surgical tool 3600 may include, for example, the exposed portion of the end effector 3660, the proximal transducer mounting portion 3620, surfaces or other features. Other surfaces may be untouched, or at most rough-shaped. Examples of such unfinished portions may include a portion of the surgical tool 3600 that may be contained inside a housing of a ultrasound medical system incorporating the surgical tool 3600.

Further fabrication steps may include removing material from the thickness of the part by machining, skiving, forming, coining, forging, or other methods known in the art. This additional machining may be performed on only one side or the surgical tool 3600 or on opposing sides of the surgical tool 3600. Such additional machining to adjust the thickness of the surgical tool 3600 may be used to form a gain feature 3655 to modify the amplitude of the mechanical wave induced in the surgical tool 3600 by the activated piezoelectric transducers driving with it. In some aspects, the gain features 3655 may be fabricated starting at a location proximal to an antinode and ending at a location distal to the antinode. The fabricated gain features 3655 may incorporate regions of high mechanical gain of the waveguide 3610 thereby minimizing the part-to-part variation in gain. The resulting thickness of the part by removal or reduction may yield a section of the surgical tool 3600 that is at or near the lower end of the standard sheet thickness tolerance.

Typical thickness tolerance on sheet stock materials such as sheet titanium or aluminum may be about +/−0.0080 inches or +/−0.203 mm. This tolerance is roughly four to eight times that which may be found in ultrasonic surgical tools machined via precise turning operations (e.g., lathe, Swiss screw machine, etc.). The displacement gain through a waveguide 3610 is related to changes in cross sectional area of the member. Therefore, large variation in the lateral aspects of a transmission member (such as thickness variation) may result in large part-to-part variation in displacement gain. Therefore, precision tuning of the displacement gain between surgical tools may be accomplished through such additional machining. It may be recognized that changes in area at or near antinodes of vibration have little to no effect on displacement gain, while changes in area at or near nodes of vibration have maximal effect on displacement gain.

Figure 37:
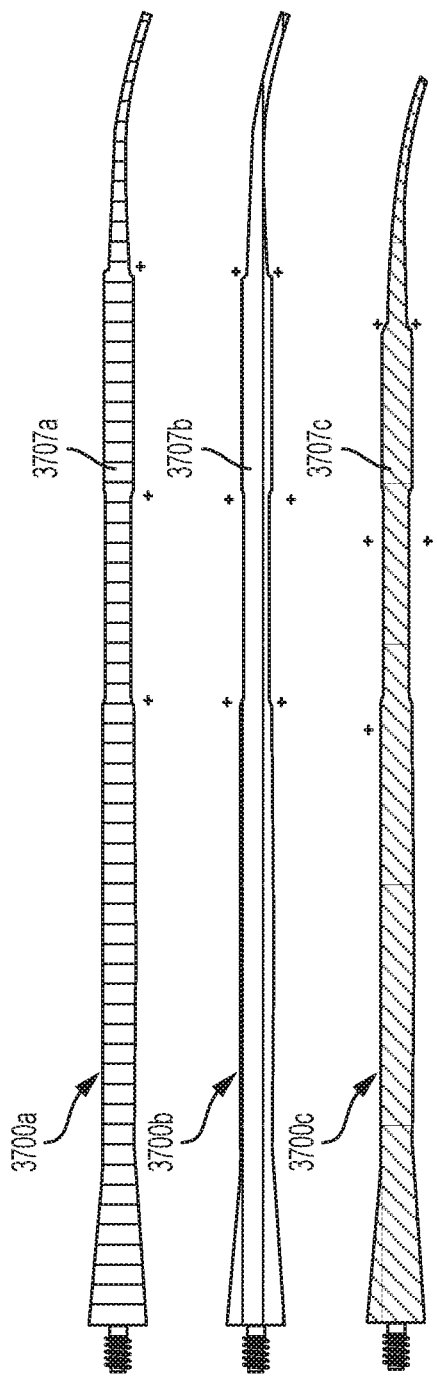
FIG. 37 is a plan view of surgical tools depicting the metal grain orientation of the surgical tools, according to one aspect of this disclosure.

As disclosed above, precision tuning of the displacement gain between surgical tools may be accomplished through appropriate precision machining of a surgical tool. An additional manner to tune the vibrational characteristics of a surgical tool may be to fabricate the surgical tool in a specified direction with respect to the grain orientation of the sheet stock from which it is manufactured, specifically orienting a longitudinal axis of the tool with respect to the grain orientation of the sheet stock. FIG. 37 illustrates surgical tools 3700a-c that may be machined according to the grain pattern of the sheet stock from which they are manufactured. Thus, surgical tool 3700a is fabricated having a transverse grain pattern 3707a, in which the longitudinal axis of the surgical tool 3700a is oriented orthogonal to the grain direction. Surgical tool 3700b is fabricated to have a longitudinal grain pattern 3707b, in which the longitudinal axis of the surgical tool 3700b is oriented parallel to the grain direction. Surgical tool 3700c is fabricated to have the longitudinal axis of the surgical tool 3700c oriented in another direction with respect to the grain orientation. In some applications, the longitudinal axis of the surgical tool is oriented at an angle with respect to the grain direction to minimize stress in at least a portion of the surgical tool upon activation. In other applications, the longitudinal axis of the surgical tool is oriented at an angle with respect to the grain direction to maximize a longitudinal deflection of the surgical tool upon activation.

The properties of such surgical tools, based on samples fabricated from titanium alloy Ti6Al4V ELI have been determined as follows. A surgical tool 3700a, having a transverse grain 3707a may have a stiffness, E=18,520,000 PSI 55.5 and a quarter-wave length (at 55.5 kHz)=0.952 inches. A surgical tool 3700b, having a longitudinal grain 3707b may have a stiffness, E=16,310,000 PSI, and a quarter-wave length (at 55.5 kHz)=0.894 inches. These values may be compared to un-oriented rod stock which may have a stiffness, E=15,680,000 PSI a quarter-wave length (at 55.5 kHz)=0.876 inches. The choice of grain orientation for a surgical tool may help maximize the end effector length by minimizing the error in perpendicularity from the centerline of the end effector to the grain direction. For example, a transverse grain orientation 3707a may result in a minimal error (theoretically zero) and maximum length for a surgical tool having a straight end effector (i.e., no curve). Alternatively, a choice of grain orientation for a surgical tool may help minimize the end effector length by maximizing the error in perpendicularity from the centerline of end effector to the grain direction Additionally, the choice of grain orientation may help reduce stress if the grain orient permits increased wavelength in high stress areas In some fabricated samples, surgical tools fabricated having longitudinal and transverse grain orientations have demonstrated acoustic function. In some fabricated samples, surgical tools having curved end effectors with transverse grains have demonstrated acoustic and vessel sealing function.

Figure 38:
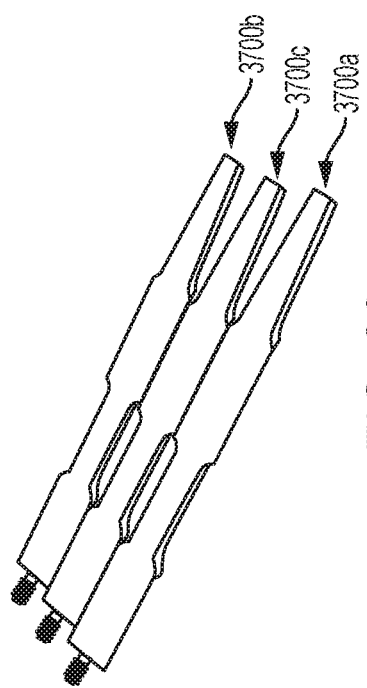
FIG. 38 is a perspective view of the surgical tools depicted in FIG. 37, according to one aspect of this disclosure.

FIG. 38 depicts the surgical tools 3700a-c of FIG. 37 illustrating that the length of a surgical tool may be optimized based on the grain orientation of the metal comprising the surgical tools. As disclosed above, a surgical tool 3700a having a transverse grain 3707a may have a longer resonance quarter wavelength by about 0.06 inches than a surgical tool 3700b having a longitudinal grain 3707b (when activated at 55.5 kHz). It may be understood that more precise tuning of a surgical tool may be accomplished in this manner.

Figure 39:
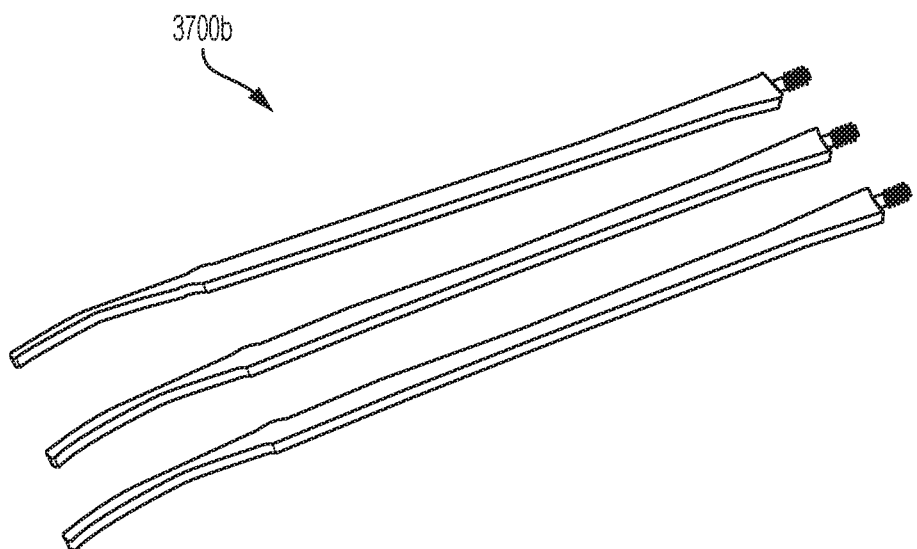
FIG. 39 is a perspective view of additional surgical tools depicted in FIG. 37, according to one aspect of this disclosure.
Figure 40:
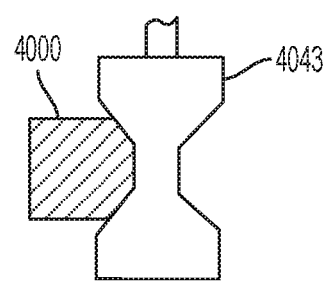
FIG. 40 is a side view of an additional fabrication step of a surgical tool, according to one aspect of this disclosure.

FIG. 39 illustrates a surgical tool 3700b having a longitudinal grain. Additional performance tuning may be provided by additional machining of a face of the surgical tool (as opposed to machining the edges of the tool as indicated in FIG. 36). Further performance tuning, for example of the displacement amplitude of the surgical tool, is depicted in FIG. 40. In FIG. 40, the cross-section of the waveguide 4000 optionally may be routed (milled), using a side or end mill 4043, into an octagonal or more rounded shape using a single pass on each of two opposite sides, possibly at the same time, in order to reduce the required instrument shaft diameter.

As disclosed above with respect to FIGS. 36-40, a variety of mechanical fabrication steps may be considered for optimizing the price and performance of a surgical tool. Thus, minimizing the number of finishing steps may result in well-performing surgical tools without resorting to costly, but unnecessary, additional steps added for purely aesthetic reasons. The surgical tool may be manufactured at a predetermined angle with respect to the flat stock grain, thereby optimizing the length or stiffness of the resultant tool. Reproducibility of performance between multiple surgical tools fabricated from flat stock may be accomplished through machining ("shaving") small amounts of mass from the tools to overcome variability in flat stock thickness and to improve inter-tool tolerance. Additionally, fabrication steps may be included to tune the mechanical displacement (or gain) of the surgical tool.

Figure 41:
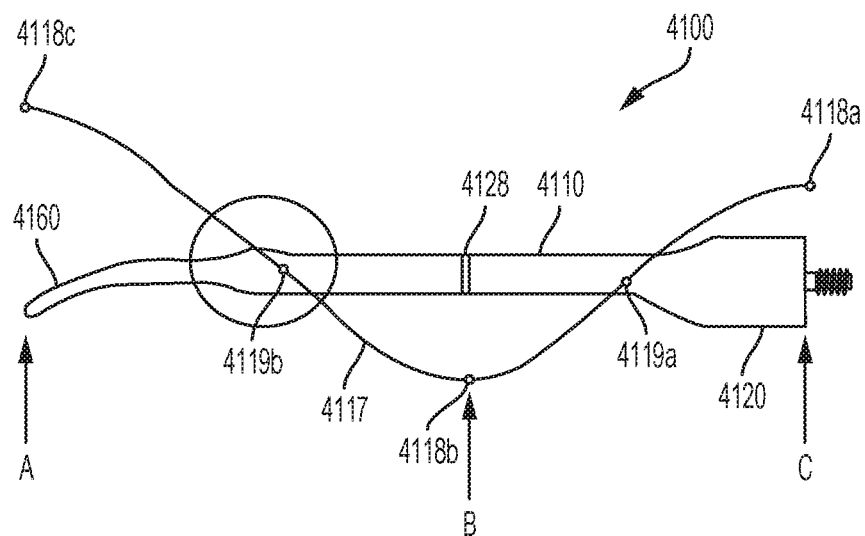
FIG. 41 is a plan view of the surgical tool depicted in FIG. 32 with a superimposed illustration of a mechanical standing wave imparted to it by an activated piezoelectric transducer, according to one aspect of this disclosure.
Figure 42:
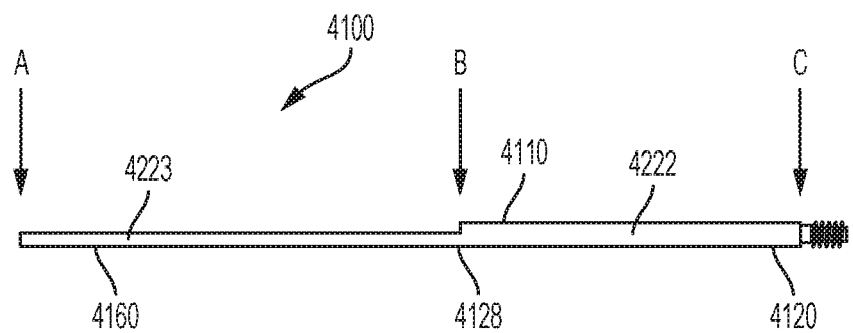
FIG. 42 is a side view of the surgical tool depicted in FIG. 41, according to one aspect of this disclosure.

FIGS. 41 and 42 illustrate a plan (FIG. 41) and edge (FIG. 42) view, respectively, of a surgical tool 4100 machined to preferentially increase the mechanical displacement of an end effector 4160. Surgical tool 4100, as illustrated, comprises a transducer mounting portion 4120, and end effector 4160, and a waveguide 4110 disposed therebetween. For comparisons between FIGS. 41 and 42, indicia A and C correspond to the most distal end of the end effector 4160 and the most proximal terminal end of the transducer mounting portion 4120, respectively. Overlaid on the image of the surgical tool 4100 is a mechanical standing wave 4117 that may be induced in the surgical tool 4100 when it vibrates due to an induced mechanical wave from a piezoelectric transducer contacting the transducer mounting portion 4120 of the surgical tool 4100. The standing wave 4117 may be induced in the surgical tool 4100 through the activation of one or more transducers in mechanical communication with the surgical tool 4100 by an electrical signal having a predetermined frequency component. The standing wave 4117 may have a wavelength proportional to the predetermined frequency component of the electrical signal. The standing wave 4117 may be effectively sinusoidal, and characterized by nodes 4119a,b and antinodes 4118a,b,c. Without being bound by theory, the nodes 4119a,b may represent locations of the surgical tool that undergo minimal mechanical displacement, and the antinodes 4118a,b,c may represent locations demonstrating a maximal absolute mechanical displacement of the surgical tool 4100. Solely for descriptive purposes with respect to FIG. 41, antinode 4118a may be termed the proximal antinode, antinode 4118b may be termed the medial antinode, and antinode 4118c may refer to the distal antinode. Again, for purposes of comparison between FIGS. 41 and 42, indicium B may correspond to the location of the medial antinode 4118b. The medial antinode 4118b may be located in the surgical tool 4100 at medial antinode location 4128.

The amount of mechanical displacement of any portion of an activated surgical tool 4100 may depend on a number of factors including the amount of power supplied to the piezoelectric transducers, the local geometry at the portion of the surgical tool 4100 and the local mass of the portion of the surgical tool 4100. Again, without being bound by theory, the mechanical displacement of a portion of an activated surgical tool may vary inversely with mass (controlling for piezoelectric transducer power and local geometry). In FIG. 41, the thickness of the surgical tool 4100 is decreased, thereby reducing the mass, distal to the medial antinode location 4128. This is made clear in FIG. 42, in which the thickness 4222 of the proximal end of the surgical tool 4100 (corresponding to the tool from the medial antinode location 4128 to the proximal end of the tool at indicium C) is greater than the thickness 4223 of the distal end of the surgical tool 4100 (corresponding to the tool from the medial antinode location 4128 to the distal end of the tool at indicium A). As a result, the mechanical displacement of the end effector 4160 corresponding to the distal antinode 4118c may be greater than the displacement of the surgical tool 4100 at other antinodes, such as at antinodes 4118a,b. Such a fabrication technique may be useful to create a surgical tool 4100 with a greater amount of mechanical displacement at the end effector 4160 than at the locations of other anti-node 4118a,b throughout the surgical tool. 4100.

In general, additional fabrication steps of a surgical tool may include lateral or side machining, or surface machining (or a combination of the two). Fabrication methods that may be directed to machining the lateral or side surfaces of a surgical tool may result in a short and wide blade design. The lateral machining processes may be used to create a curved blade tip of an end effector. The face of the surgical tool, derived from the surface of the flat stock from which it is fabricated, may then become a clamping surface for a shear-type device. After such lateral machining steps, changes to vertical dimensions (for example, vertical tapering) may be created using additional process (for example, coining). Additional features in the surgical tool that may be created by lateral machining processes may include a vertical ribbon section to allow horizontal articulation, lateral steps in the waveguide to adjust the gain in mechanical deflection, and lateral offsets that may be used to create clearance of vertical structures. Fabrication methods that may be directed to machining the face or transverse surface may result in a long and skinny blade design. The transverse surface machining processes may be used to create a vertical profile of the blade tip (for example, a vertically tapered tip). The machined transverse faces may become a clamping surface for a shear-type device and the vertical machined profiles may result in an end effector having improved clamping pressure profile or any improved gripping capability, useful for clamping wet tissue. After such surface machining steps, changes to the lateral dimension (for example, curve, lateral tapering) may be created using additional process (for example, forming). Additional features in the surgical tool that may be created by transverse surface machining processes may include a horizontal ribbon section to allow vertical articulation, vertical steps in the waveguide to adjust the gain in mechanical deflection, and vertical offsets that may be used to create clearance of horizontal structures such as a waveguide that terminates with straight lateral structures, such as clamp arm pivot pins. Combinations of both lateral and transverse machining steps may be used to create a surgical tool having more complex geometries, for example one having a waveguide and/or end effector consisting of curve(s), or any number of centerlines.

Figure 43:
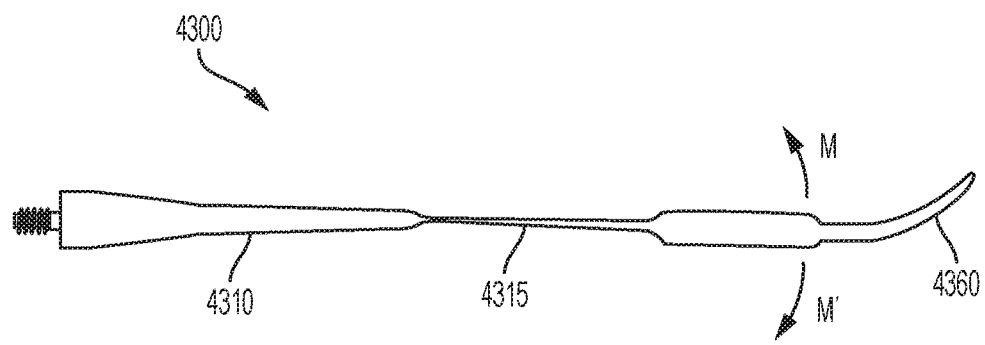
FIG. 43 is a plan view of a surgical tool configured to be displaced in a side-way manner, according to one aspect of this disclosure.
Figure 44:
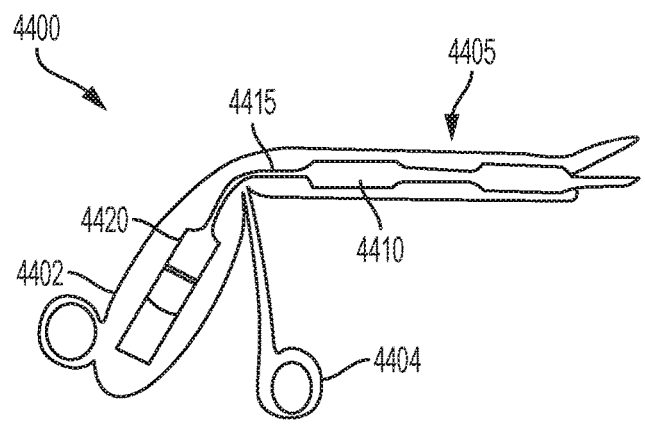
FIGS. 44 and 45 illustrate hand actuated ultrasonic medical devices, according to one aspect of this disclosure.

FIG. 43 illustrates a side view of a surgical device 4300 having a waveguide 4310 and an end effector 4360. As depicted, the waveguide 4310 may include horizontal ribbon section 4315 that may be machined using transverse machining processes as disclosed above. The resulting surgical device 4300 is thereby configured to articulate in directions M and M' about the horizontal ribbon section 4315 in the vertical cutting plane. Additional lateral machining may impart a vertical taper to the end effector 4360. FIG. 44 illustrates a hand-held ultrasound medical system 4400 incorporating a surgical tool 4405 (shown in plan view) having a transducer mounting portion 4420, and end effector, and a waveguide 4410 therebetween. In the aspect of FIG. 44, the ultrasound medical system 4400 may include a housing 4402 and a clamping actuator 4404. The hand-held ultrasound medical system 4400 may incorporate such electronics and power sources (such as one or more batteries) to control the activation of the surgical tool 4405 thereby allowing the ultrasound medical system 4400 to operate without requiring an external ultrasound power source. The waveguide 4410 may include a vertical ribbon section 4415 that may be machined using lateral machining processes as disclosed above. The surgical tool 4405 may be fabricated using lateral machining methods to form the upper and lower surface of the end effector. Vertical tapering of the end effector may require one or more additional transverse surface machining processes. The surgical tool 4405 is thus configured to articulate about the vertical ribbon section 4415 orthogonal to the vertical cutting plane.

Figure 45:
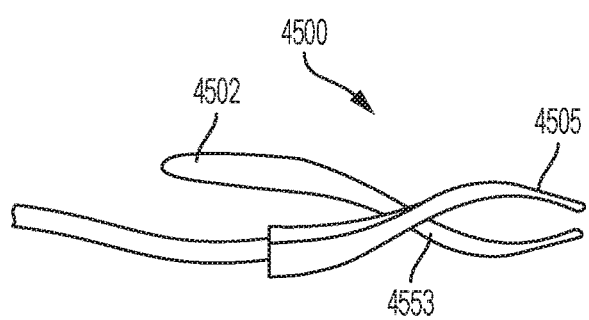
Figure 46:
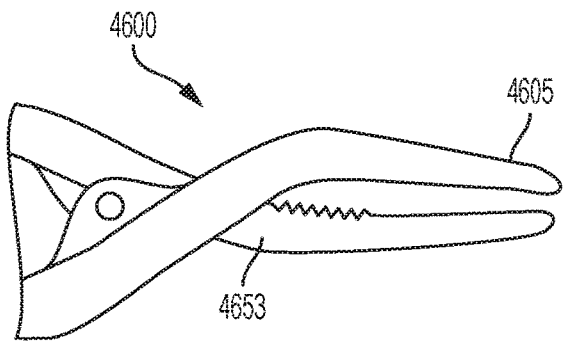
FIG. 46 illustrates the effector end of the hand actuated ultrasonic medical device of FIG. 45, according to one aspect of this disclosure.

In many of the aspects disclosed above, a surgical tool may be a cutting tool in which the end effector comprises a blade designed for cutting a tissue. However, with additional or alternative fabrication steps, the surgical tool may become a clamping or clamping-plus-cutting tool. FIGS. 45 and 46 illustrate hand-held ultrasound medical systems that may incorporate clamping functions. The ultrasound medical system 4500 depicted in FIG. 45 may be a clamping device including a clamping actuator 4502 that may control the position of a clamp jaw 4553 with respect to the distal end 4505 of the surgical tool. The distal end 4505 of the surgical tool may be fabricated to have a complementary shape to the clamp jaw 4553. For example, the distal end 4505 may have a waveguide including an angled portion immediately proximal to a straight end effector, thereby allowing precision working at the end effector. FIG. 46 depicts another example of an ultrasound medical system 4600 that is similarly configured for tissue clamping as opposed to tissue cutting. In the example of FIG. 46, the clamp jaw 4653 may have a complementary shape to the distal end 4605 of the surgical tool. Thus, the distal end 4605 may have a curved waveguide portion immediately proximal to a straight end effector having a flat clamping surface to mate with the end of the clamp jaw 4653.

FIGS. 47-57 are directed to mechanisms by which a surgical tool may be attached to an ultrasonic system (such as depicted in FIG. 1) or ultrasound medical system (such as depicted in FIGS. 34, 35, and 44-46), or any other medical device configured to use ultrasonic vibration to effect a therapeutic result. Such a surgical tool, for example, may be fabricated from sheet stock, although alternative examples of such a surgical tool may be fabricated from round stock or bar stock. Such a surgical tool may also be a component of an ultrasonic medical device that includes one or more piezoelectric transducers affixed onto a transducer mounting portion of the surgical tool.

Figure 47:
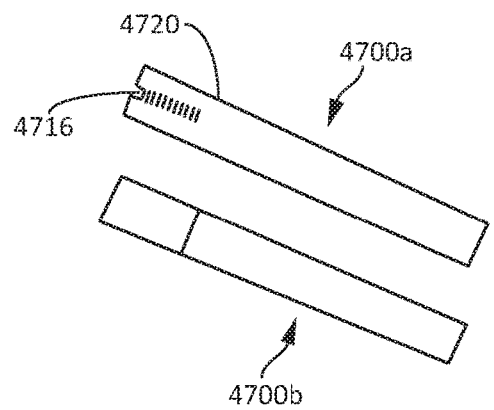
FIG. 47 illustrates a plan view of two surgical tools having female threads machined in the transducer mounting portion, according to one aspect of this disclosure.
Figure 48:
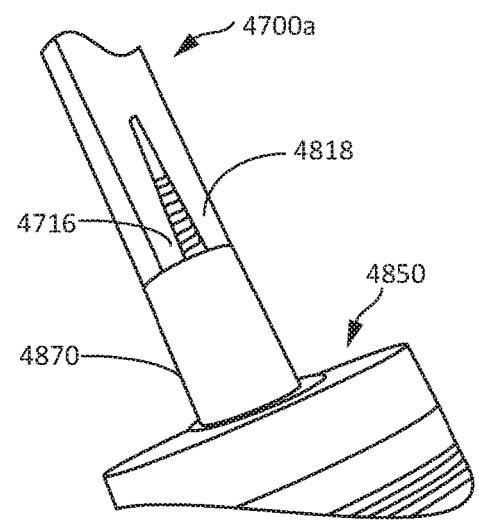
FIG. 48 is a perspective view of a transducer mounting portion of the surgical tool of FIG. 47 mounted in an ultrasonic medical device, according to one aspect of this disclosure.
Figure 49:
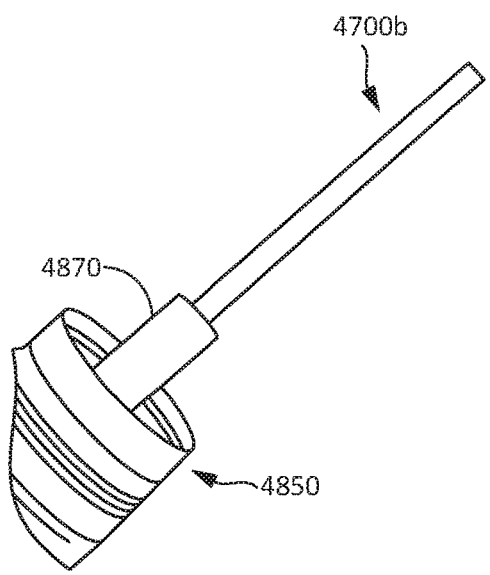
FIGS. 49 and 50 are a side view and a perspective view, respectively, of the two surgical tools of FIG. 47 mounted in the ultrasonic medical device of FIG. 48, according to one aspect of this disclosure.
Figure 50:
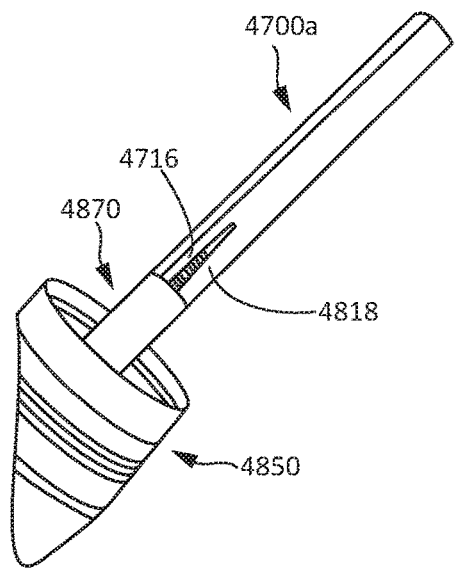

FIGS. 47-53 depict a surgical tool 4700 having female threads 4716 machined into a transducer mounting portion 4720. FIG. 47 depicts a surgical tool 4700a fabricated from sheet stock having a thickness of about 0.100" and a surgical tool 4700b fabricated from sheet stock having a thickness of about 0.125". Both surgical tools 4700a,b have a 4-40 threaded hole tapped along a longitudinal axis of the surgical tools 4700a,b. It may be noted that a component having a male thread configured to mate with the 4-40 threaded hole may have a major dimension of about 0.110". Thus, the female threads 4716 extend beyond the surfaces of the surgical tool 4700a because the male threads may extend laterally beyond the surfaces of the surgical tool 4700a. FIG. 48 illustrates an assembled ultrasonic medical device 4850 including the surgical tool 4700a, a collet, clamp or collar 4870 configured to secure the surgical tool 4700a, and a threaded male component 4818 inserted into the female threads 4716 of the surgical tool 4700a. FIG. 49 illustrates a side view of an assembled ultrasonic medical device 4850 including the surgical tool 4700b, and a collet, clamp or collar 4870 configured to secure the surgical tool 4700b. In FIG. 49, the threaded male component 4818 is not visible since the surgical tool 4700b has a thickness greater than the major dimension of the threaded male component. FIG. 50 depicts another view of the assembled ultrasonic medical device 4850 of FIG. 48 in which the entirety of the surgical tool 4700a is illustrated.

Figure 51:
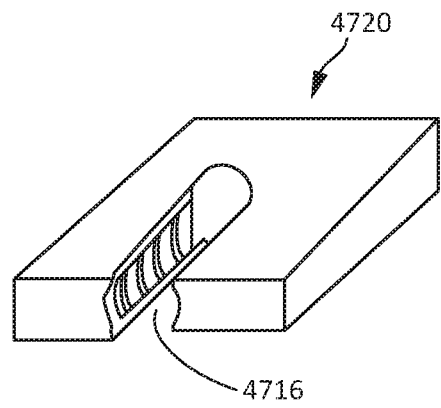
FIG. 51 is an end perspective view of the surgical device of FIG. 47, illustrating the female threads tapped into the transducer mounting portion, according to one aspect of this disclosure.
Figure 52:
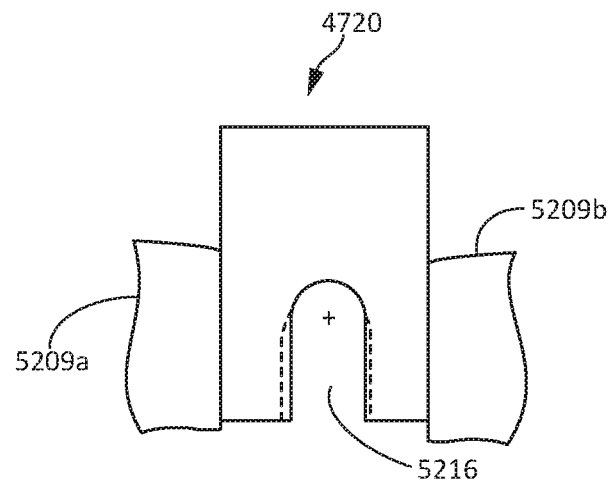
FIG. 52 is a plan view of fabricating female threads into the transducer mounting portion of the surgical tool of FIG. 47, according to one aspect of this disclosure.
Figure 53:
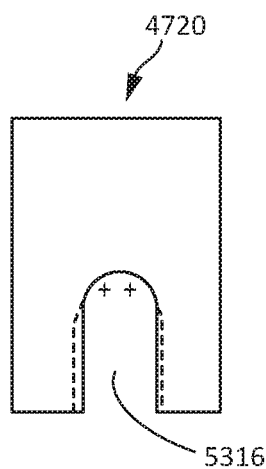
FIG. 53 is a plan view of the female threads tapped into the transducer mounting portion of the surgical tool of FIG. 47, according to one aspect of this disclosure.

FIG. 51 depicts a close-up view of the transducer mounting portion 4720 of the surgical tool 4700a illustrated in FIG. 47. The female threads 5216 are depicted as being formed along the inner surface of a hole tapped along a longitudinal axis of the surgical tool 4700a. FIG. 52 illustrates a method by which the female threads 5216 may be fabricated into the transducer mounting portion 4720 of a surgical tool such as 4700a in which the major dimension of the corresponding male thread is larger than the thickness of the surgical tool 4700a. In one method, supports 5209a,b may be braced against the lateral edges of the surgical tool 4700a. A slot may then be machined along the longitudinal axis of the surgical tool 4700a in the transducer mounting portion and the female threads 5216 may be tapped. In this manner, the transducer mounting portion of the surgical tool 4700a is not deformed during the tapping process. The slot may terminate with a radius or radii at its distal termination for reducing acoustic stresses. The radius may comprise a single radius (+ in FIG. 52) or a double radius (++ in FIG. 53).

Figure 54:
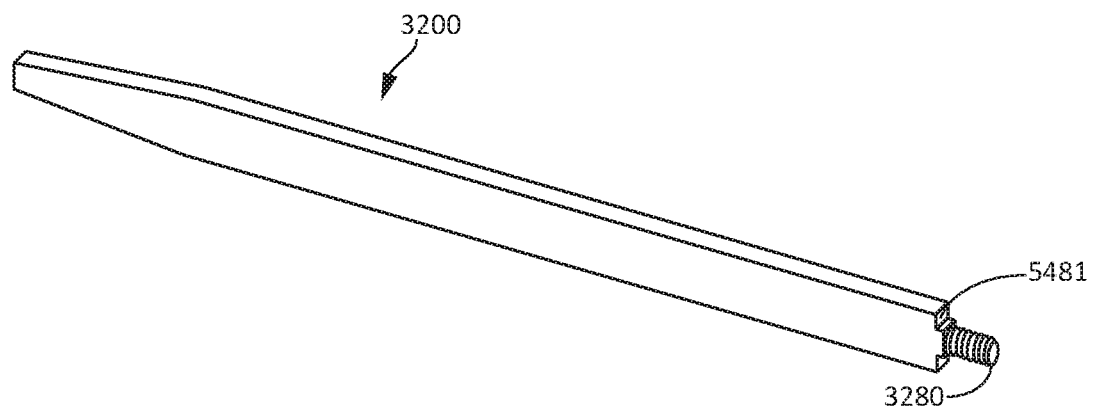
FIG. 54 is a perspective view of a surgical tool including a threaded stub at the transducer mounting portion, according to one aspect of this disclosure.

FIGS. 54-57 depict aspects of a male threaded stud or boss 3280 attached at the proximal end of a surgical tool 3200, in which the stud or boss 3280 is coaxial with a longitudinal axis of the surgical tool 3200. FIG. 54 illustrates a threaded boss 3280 having male threads having a major dimension less than or equal to the width of the surgical tool 3200. Also illustrated is a portion of a proximal surface of the surgical tool 3200 that is faced 5481 from the threaded boss. The portion of the proximal surface may be faced 5481 using a turning operation so that the faced portion 5481 is normal with respect to the longitudinal aspect of the surgical tool 3200.

Figure 55:
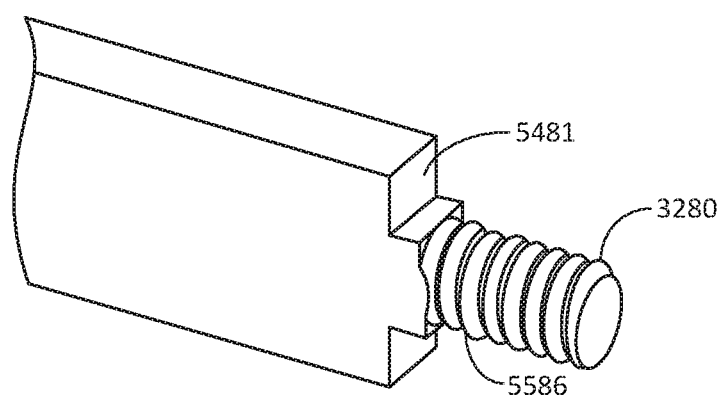
FIG. 55 is a close-up perspective view of the transducer mounting portion of the surgical tool of FIG. 54, according to one aspect of this disclosure.

FIG. 55 is a close-up view of the proximal end of the surgical tool 3200 depicted in FIG. 54. As can be observed, the threaded boss 3280 is affixed to a stand-off portion of the proximal surface and raised above the faced portion 5481 of the proximal surface. FIG. 55 also depicts the threaded boss 3280 having a male thread 5586 that possesses a major dimension greater than the width of the surgical tool 3200. The male thread may also be faced so that the portion of the male thread 5586 is reduced to the thickness of the surgical tool 3200. Such faced or machined male threads 5586 may be used to lock the threads during manufacturing for non-field-attachable/detachable products.

Figure 56:
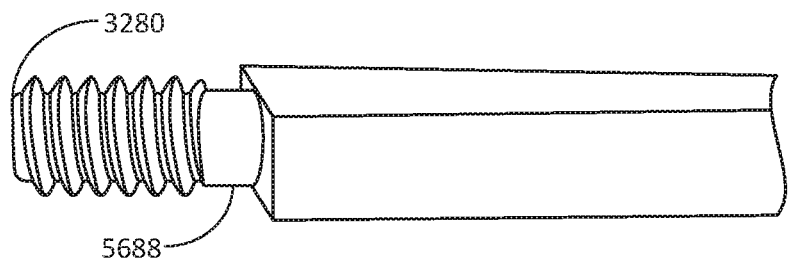
FIG. 56 is a close-up perspective view of the transducer mounting portion of a surgical tool including a threaded stub, according to one aspect of this disclosure.
Figure 57:
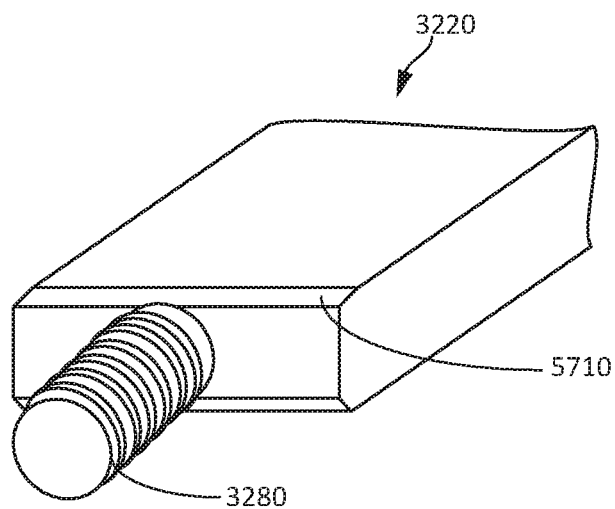
FIG. 57 is a close-up perspective view of the transducer mounting portion of a surgical tool including a threaded stub and chamfers, according to one aspect of this disclosure.

FIG. 56 depicts the proximal end of a surgical tool 3200 in which the male threads are fabricated on a boss 3280 that includes a stand-off portion 5688 that is unthreaded. FIG. 57 depicts another example of the proximal end of a surgical tool 3200 having a threaded boss 3280. In the aspect of FIG. 57, edges of proximal face include chamfers 5710 that may be fabricated by filleted, cutting, tumbling, or other appropriate methods. The use of such chamfers 5710 may be useful to prevent the edges of the proximal end of the surgical tool 3200 from "kick up a burr" on the face a mating portion of an ultrasonic medical system.

Figure 58:
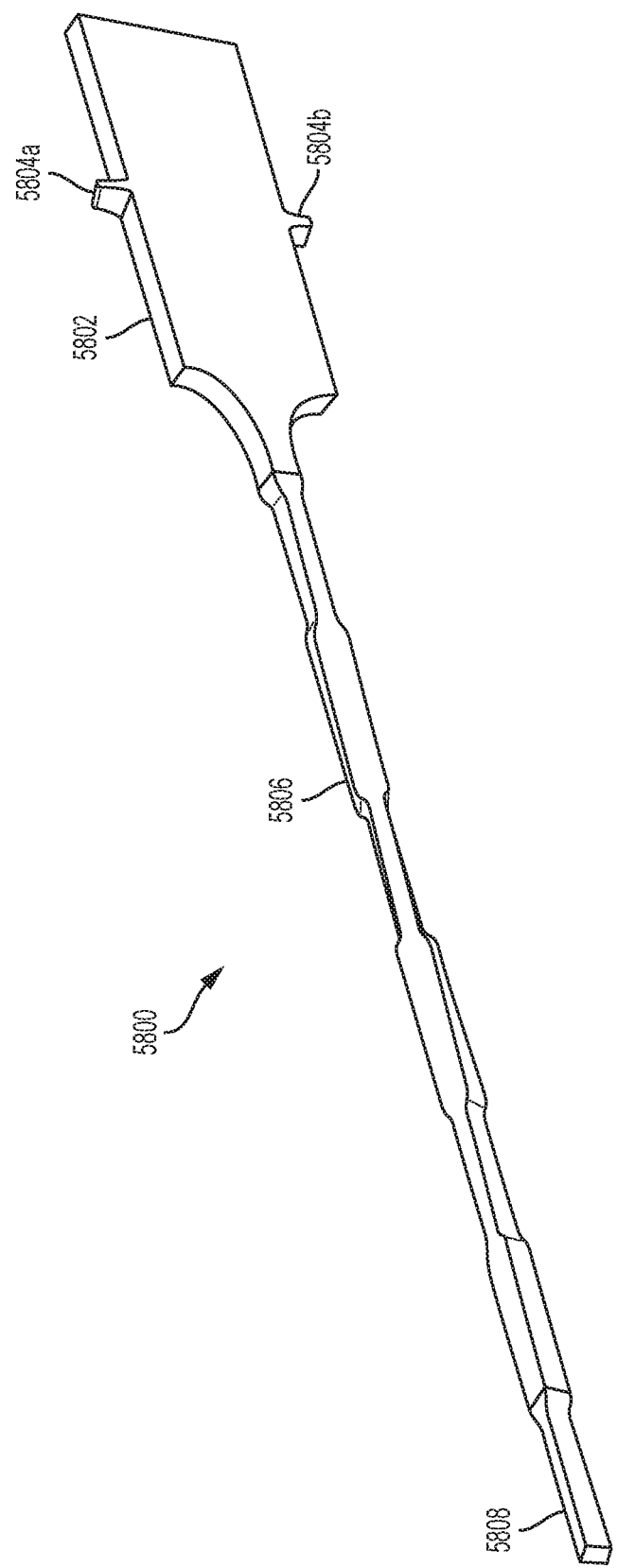
FIG. 58 is a perspective view of a surgical tool having a flat blade with a straight tip, according to one aspect of this disclosure.
Figure 59:
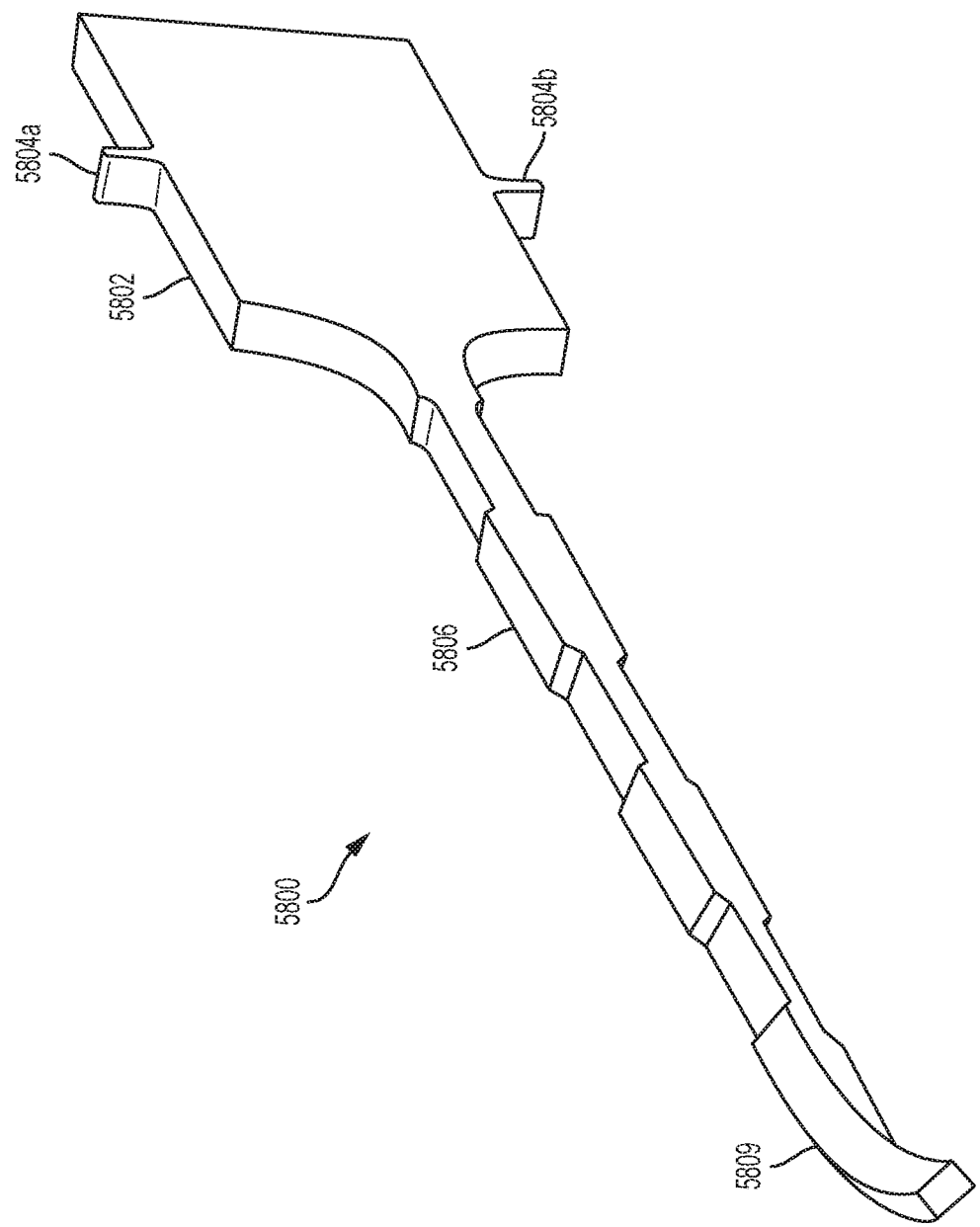
FIG. 59 is a perspective view of a surgical tool having a twisted flat blade with a curved and tapered tip, according to one aspect of this disclosure.

FIG. 58 depicts a surgical tool 5800 comprising a proximal transducer mounting portion 5802, a distal flat blade 5808 and a longitudinal portion or waveguide 5806 therebetween. The distal flat blade 5808 may comprise an end effector 5808 of the surgical tool 5800. In various aspects, referencing FIG. 36, a fabricated surgical tool 3600 or some component thereof such as the end effector 3660, may have a undesired thickness and orientation. To adjust the thickness and orientation, one or more additional manufacturing steps such as forming, machining, cutting, forging, grinding, polishing, de-burring, or tumbling may be implemented. These additional manufacturing steps may also be useful for adjusting the shape, edge quality, curvature and offset of an end effector such as the flat blade 5808. Alternatively, after using a two dimensional cutting method to form the geometry of the flat blade 5808, the flat blade 5808 may be twisted to adjust the orientation relative to a proximal feature, such as the transducer mounting portion assembly 5802. The twisting may also be used to adjust other features of the flat blade 5808, such as curvature, offset, flex section, and thin or tapered tissue clamping sections. The flat blade 5808 can be twisted at any point along its length. FIG. 59 illustrates one example of a twisted flat blade 5809 with a curved and tapered tip. The twisted flat blade 5809 is twisted for a suitable degree of rotation, such as 90 degrees, along a section of the surgical tool 5800 located between the twisted flat blade 5809 and a proximal section of the tool 5800. In some aspects, the twisted flat blade 5809 with the curved and tapered tip does not require an additional manufacturing step to adjust thickness and orientation. For example, no machining operation to form the curved and tapered tip and no forming operation to form the curvature of the twisted flat blade 5809 is necessary.

Figure 60:
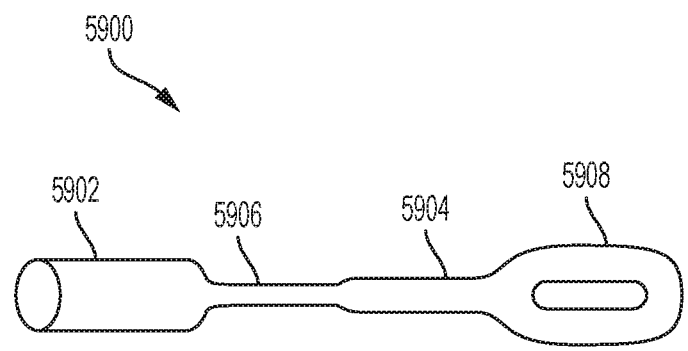
FIGS. 60-62 are plan views of surgical tools having blades with complex features, according to one aspect of this disclosure.

FIGS. 60-66 show surgical tools 5900 each comprising a proximal transducer mounting portion 5902, an ultrasonic blade 5904 with complex features 5908, 5909, 5910, 5911, 5912, 5913, 5914, 5915 and a longitudinal portion or waveguide 5906 therebetween. The blade 5904 may comprise an end effector 5904 of the surgical tool 5900. The surgical tools 5900 may be fabricated from titanium material using a metal injection molding (MIM). MIM is a net shape process for creating surgical tools with a reduction in the amount of machining required. Additionally, MIM fabricated titanium material may have similar properties to wrought titanium, such as similar stiffness, density (e.g., within 4%), and speed of sound (e.g., within 3.5%). In various aspects, MIM may be useful for fabricating ultrasonic blades with complex features. Fabricating blades with such complex features with MIM may reduce waste and cost compared to fabricating such complex blades with a conventional machining process. For example, FIG. 60 depicts a surgical tool 5900 comprising a MIM blade 5904 with a complex feature 5908 (i.e., internal hole 5908 in the ultrasonic blade 5904). The internal hole 5908 may be useful for particular surgical procedures.

Figure 61:
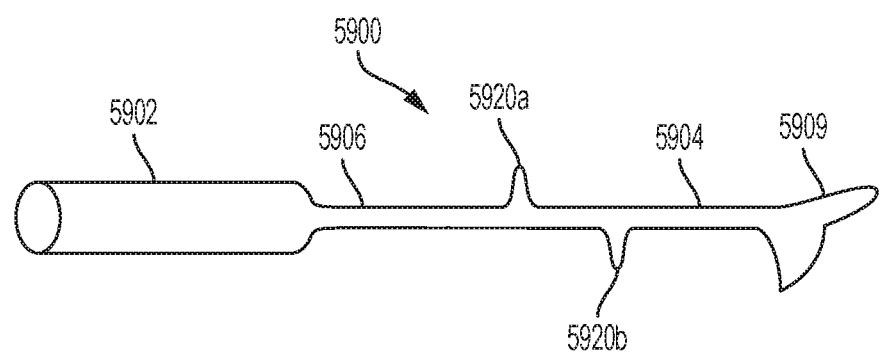
Figure 62:
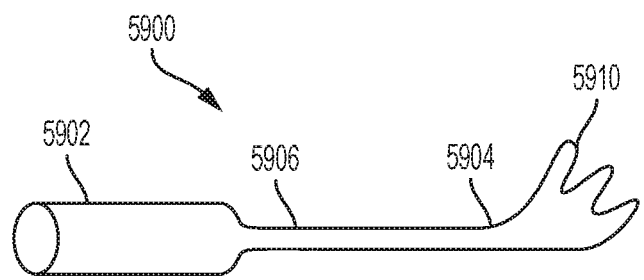
Figure 63:
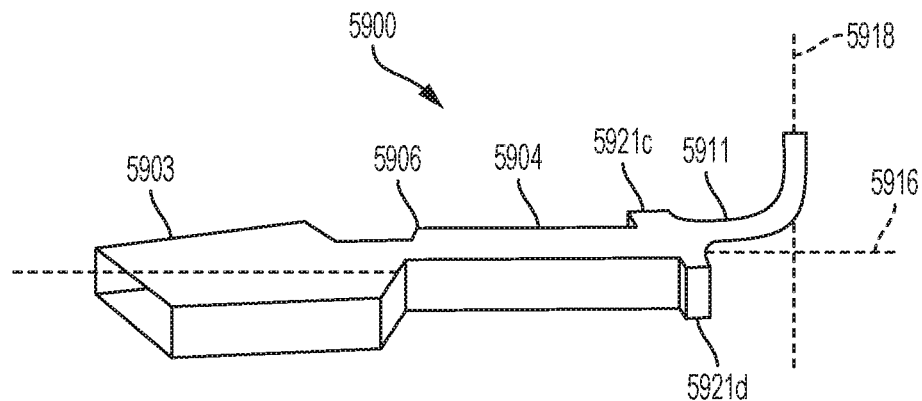
FIG. 63 is a perspective view of a surgical tool having a blade with a curved tip of large curvature, according to one aspect of this disclosure.

FIG. 61 depicts a surgical tool 5900 comprising a MIM blade 5904 with another complex feature 5909. The complex feature 5909 comprises an asymmetric design, as can be seen in FIG. 61. Specifically, the protrusions 5920a,b are disposed on opposing surface of the surgical tool 5900. For example, protrusion 5920a may be disposed on a top surface of the tool 5900 and protrusion 5920b may be disposed on a bottom surface of the tool 5900. The distal end of the MIM blade 5904 comprising the asymmetric complex feature 5909 can have a teeth type configuration. Such teeth type configurations may be particularly advantageous for cutting tissue in a surgical procedure. FIG. 62 depicts a surgical tool 5900 comprising a MIM blade 5904 with a third complex feature 5910. The complex feature 5910 comprises a finger type configuration. As can be seen in FIG. 62, the complex feature 5910 includes three fingers or prongs and can be similar to a three pronged fork. Such finger type configurations may be particularly advantageous for gripping tissue for cutting in a surgical procedure. FIG. 63 shows a surgical tool 5900 comprising a MIM blade 5904 with a large curved tip 5911. The large curvature of the blade tip 5911 protrudes in two dimensions. For example, the curved blade tip 5911 extends along both the x axis 5916 and the y axis 5918. The protrusions 5921c,d may form attachment features of the MIM blade 5904. Using MIM to fabricate a blade tip with such a large curvature can result in reduced manufacturing costs and waste. In contrast to MIM, two alternative approaches of using a larger stock to machine the large curvature into a blade or forming the curvature after fabricating a curved blade both generate waste compared to a MIM fabrication process.

Figure 64:
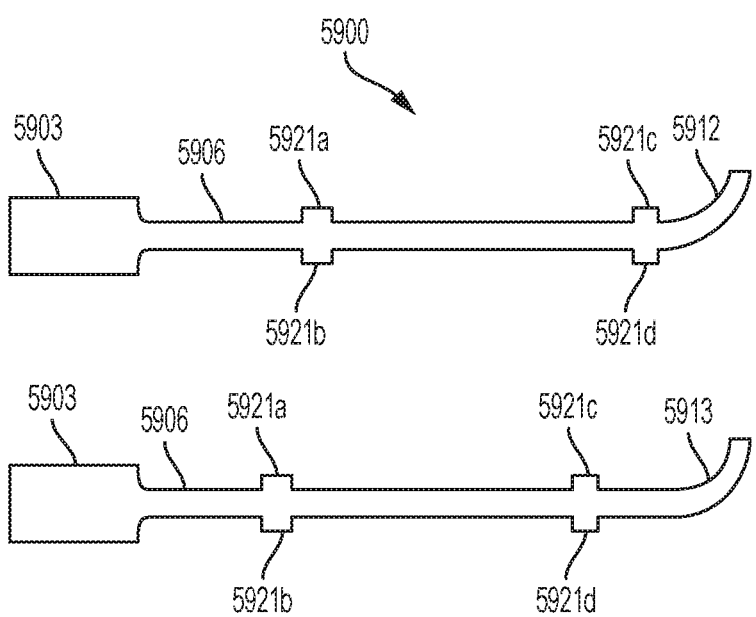
FIG. 64 is a plan view of surgical tools having blades with curved tips, according to one aspect of this disclosure.

FIG. 64 shows two surgical tools 5900 comprising blades 5904 with curved tips of varying curvatures. As can be seen in FIG. 64, the curvature of the curved blade tip 5913 is greater than the curvature of the curved blade tip 5912. The curved blade tip 5913 with greater curvature corresponds to an MIM fabricated blade 5904 while the curved blade tip 5912 with lesser curvature corresponds to a non-MIM fabricated blade 5904. The blades 5904 each have protrusions 5921c,d, which may form attachment features of the blades 5904. The tool 5900 also has attachment features

Figure 65:
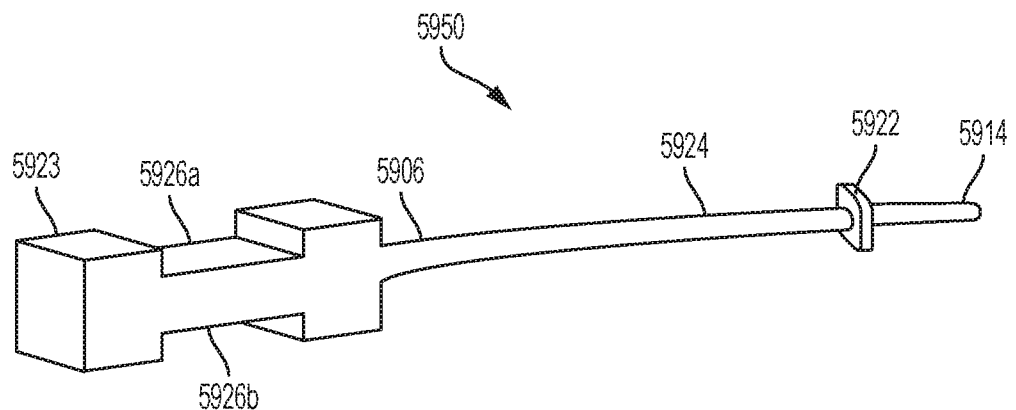
FIG. 65 is a perspective view of a surgical tool having a transducer mounting portion with a wide and flat surface, according to one aspect of this disclosure.
Figure 66:
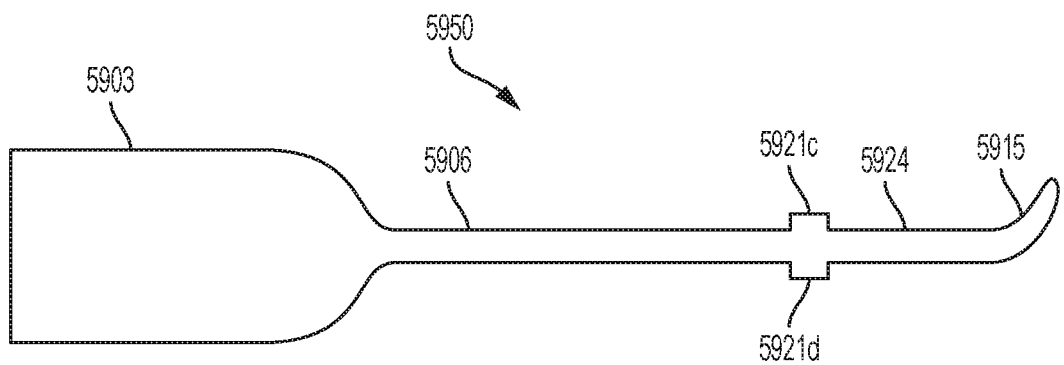
FIG. 66 is a plan view of a surgical tool having a transducer mounting portion with a wide and flat surface, according to one aspect of this disclosure.

5921*a,b*. FIG. 65 shows a surgical tool 5950 with a MIM fabricated blade 5924 that is configured for use in a D31 mode, as described previously. The surgical tool 5950 may be particularly advantageous for D31 use because the proximal transducer mounting portion 5923 comprises a square geometry with a wide and large flat surface while the blade 5924 comprises a round geometry. The transducer mounting portion 5923 also comprises grooves 5924*a,b* for receiving transducers such as transducers 312*a,b*, in an interference fit. The interference fit may comprise a heating process to press fit the transducers into the grooves 5924*a,b*, which may be undersized. Additionally, the MIM fabricated blade 5924 has a small round blade tip 5914 for effecting cutting of tissue. The blade 5924 also comprises a square guard 5922. FIG. 66 depicts a surgical tool 5950 comprising a proximal transducer mounting portion 5923 with a wide and flat surface. The MIM fabricated blade 5924 of the surgical tool 5950 comprises a curved small round blade tip 5915 for effecting cutting of tissue. The blade 5924 also comprises protrusions 5921*c,d*, which may form attachment features of the blade 5924.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic medical device comprising: a surgical tool comprising a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; a first transducer comprising a body defining a face; and a second transducer comprising a body defining a face; wherein the face of the first transducer is in mechanical communication with the first face of the surgical tool and the face of the second transducer is in mechanical communication with the second face of the surgical tool opposite the first transducer; wherein the first transducer and the second transducer are configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

Example 2

The ultrasonic medical device of Example 1, wherein the surgical tool comprises a metal having a grain direction oriented at an angle with respect to the longitudinal axis.

Example 3

The ultrasonic medical device of Example 1 or Example 2, wherein the longitudinal axis of the surgical tool is oriented parallel to the grain direction.

Example 4

The ultrasonic medical device of one or more of Example 2 through Example 3, wherein the longitudinal axis of the surgical tool is oriented orthogonal to the grain direction.

Example 5

The ultrasonic medical device of one or more of Example 2 through Example 4, wherein the longitudinal axis of the surgical tool is oriented at an angle with respect to the grain direction to minimize stress in at least a portion of the surgical tool upon activation.

Example 6

The ultrasonic medical device of one or more of Example 2 through Example 5, wherein the longitudinal axis of the surgical tool is oriented at an angle with respect to the grain direction to maximize a longitudinal deflection of the surgical tool upon activation.

Example 7

The ultrasonic medical device of one or more of Example 1 through Example 6, wherein the body of the first transducer is disposed symmetrically about a node location of the surgical tool.

Example 8

The ultrasonic medical device of Example 7, wherein a body of the second transducer is disposed symmetrically about the node location in the surgical tool.

Example 9

The ultrasonic medical device of Example 8, wherein the face of the second transducer is fixed to the second face of the surgical tool with the conductive adhesive at the node location in the surgical tool and with a high strength adhesive at a location distant from the node location in the surgical tool.

Example 10

The ultrasonic medical device of one or more of Example 7 through Example 9, wherein the face of the first transducer is fixed to the first face of the surgical tool with an electrically conductive adhesive at the node location and wherein the face of the first transducer is fixed to the first face of the surgical tool with a high strength adhesive at a location away from the node location.

Example 11

The ultrasonic medical device of one or more of Example 1 through Example 10, further comprising a third transducer and a fourth transducer, each of the third and fourth transducer comprising a body defining a face.

Example 12

The ultrasonic medical device of Example 11, wherein the third transducer is in mechanical communication with a second face of the first transducer and the fourth transducer is in mechanical communication with a second face of the second transducer.

Example 13

The ultrasonic medical device of Example 12, wherein the third transducer is smaller than the first transducer.

Example 14

The ultrasonic medical device of Example 13, wherein the fourth transducer is smaller than the second transducer.

Example 15

The ultrasonic medical device of one or more of Example 11 through Example 14, wherein a face of the third transducer is in mechanical communication with the first face of the surgical tool and a face of the fourth transducer is in mechanical communication with the opposing face of the surgical tool and opposite the third transducer, and wherein the third transducer is disposed along the waveguide of the surgical tool relative to the first transducer and the fourth transducer is disposed along the waveguide of the surgical tool relative to the second transducer.

Example 16

The ultrasonic medical device of Example 15, wherein the first transducer and the third transducer are disposed longitudinally symmetrically about the node location in the surgical tool and the second transducer and the fourth transducer are disposed longitudinally symmetrically about the node location in the surgical too.

Example 17

The ultrasonic medical device of Example 16, wherein the first transducer is disposed proximate to the third transducer along the waveguide and the second transducer is disposed proximate to the fourth transducer along the waveguide.

Example 18

The ultrasonic medical device of one or more of Example 1 through Example 17, wherein the first transducer comprises a first planar array of first transducer plates and the second transducer comprises a second planar array of second transducer plates, wherein each of the first transducer plates and each of the second transducer plates is independently activatable by an electrical signal having a predetermined frequency component.

Example 19

The ultrasonic medical device of one or more of Example 1 through Example 18, further comprising a clip configured to apply a compression force to each of the first transducer and the second transducer against the surgical tool.

Example 20

The ultrasonic medical device of one or more of Example 1 through Example 19, further comprising a clip configured to apply a longitudinal compression force to the first transducer.

Example 21

The ultrasonic medical device of one or more of Example 1 through Example 20, wherein at least a portion of the waveguide of the surgical tool distal to the first transducer and the second transducer has a rectangular cross section.

Example 22

The ultrasonic medical device of one or more of Example 1 through Example 21, wherein the rectangular cross-section is a square cross-section.

Example 23

The ultrasonic medical device of one or more of Example 1 through Example 22, wherein at least a portion of the waveguide of the surgical tool distal to the first transducer and the second transducer has an elliptical cross section.

Example 24

The ultrasonic medical device of one or more of Example 1 through Example 23, wherein the elliptical cross section is a circular cross section.

Example 25

The ultrasonic medical device of one or more of Example 1 through Example 24, further comprising a housing, wherein at least a portion of the surgical tool is disposed within the housing.

Example 26

The ultrasonic medical device of Example 25, wherein the surgical tool further comprises a first flange and a second flange, wherein the first flange extends from a first side of the surgical tool and the second flange extends from an opposing side of the surgical tool, wherein each of the first flange and the second flange is symmetrically disposed about a node location in the surgical tool, wherein the housing comprises a first retainer and a second retainer, and wherein the first retainer is configured to receive the first flange and the second retainer is configured to receive the second flange.

Example 27

The ultrasonic medical device of one or more of Example 25 through Example 26, wherein the housing comprises a pair of electrical contacts, wherein a first electrical contact of the pair of electrical contacts is configured to contact an electrically conductive portion of the first transducer and a second electrical contact of the pair of electrical contacts is configured to contact an electrically conductive portion of the second transducer.

Example 28

The ultrasonic medical device of Example 27, wherein the first contact is configured to provide a compression force to the first transducer against the surgical tool and the second contact is configured to provide a compression force to the second transducer against the surgical tool.

Example 29

The ultrasonic medical device of one or more of Example 27 through Example 28, wherein the first contact is configured to provide an electrical contact with the first transducer and the second contact is configured to provide an electrical contact with the second transducer.

Example 30

The ultrasonic medical device of one or more of Example 1 through Example 29, further comprising a plurality of female screw threads fabricated into the proximal end of the surgical tool and oriented along a longitudinal axis thereof.

Example 31

The ultrasonic medical device of Example 30, wherein the plurality of female screw threads are configured to receive a component having mating male threads that have a major dimension less than or equal to a thickness of the surgical tool, wherein the thickness comprises a distance between the first face of the surgical tool and the second face of the surgical tool.

Example 32

The ultrasonic medical device of one or more of Example 30 through Example 31, wherein the plurality of female screw threads are configured to receive a component having mating male threads that have a major dimension greater than a thickness of the surgical tool, wherein the thickness comprises a distance between the first face of the surgical tool and the second face of the surgical tool.

Example 33

The ultrasonic medical device of one or more of Example 1 through Example 32, further comprising a boss extending in a proximal direction from the proximal end of the surgical tool and oriented along a longitudinal axis thereof, and wherein the boss comprises a plurality of male screw threads.

Example 34

The ultrasonic medical device of Example 33, wherein a portion of the plurality of male screw threads have a major dimension less than or equal to a thickness of the surgical tool, wherein the thickness comprises a distance between the first face of the surgical tool and the second face of the surgical tool.

Example 35

A method of fabricating an ultrasonic medical device comprising: machining a surgical tool from a portion of a flat metal stock, wherein the surgical tool comprises a transducer mounting portion at a proximal end, an end effector at a distal end, and a waveguide disposed therebetween, the waveguide extending along a longitudinal axis, the transducer mounting portion of the surgical tool comprising a first face and a second face at the proximal end, the second face positioned opposite the first face; contacting a face of a first transducer with the first face of the surgical tool wherein the first transducer is configured to operate in a D31 mode with respect to the longitudinal axis of the waveguide; and contacting a face of a second transducer with the second face of the surgical tool opposite the first transduce, wherein the second transducer is configured to operate in a D31 mode with respect to the longitudinal axis of the waveguide; wherein, upon activation by an electrical signal having a predetermined frequency component, the first and second transducers are configured to induce a standing wave in the surgical tool to cause the end effector to vibrate, the standing wave having a wavelength proportional to the predetermined frequency component of the electrical signal; and wherein the surgical tool defines nodes and antinodes corresponding to the nodes and antinodes of the induced standing wave, wherein the nodes correspond to locations of minimal displacement and the antinodes correspond to locations of maximum displacement.

Example 36

The method of Example 35, wherein machining a surgical tool from a portion of a flat metal stock comprises machining a surgical tool comprising a metal having a grain direction oriented at an angle with respect to the longitudinal axis of the surgical tool thereby optimizing an operational characteristic of the surgical tool.

Example 37

The method of Example 35 or Example 36, wherein machining a surgical tool having a longitudinal axis oriented at an angle with respect to a grain direction of the flat metal stock comprises machining a surgical tool having a longitudinal axis oriented parallel to the grain direction of the flat metal stock.

Example 38

The method of one or more of Example 36 through Example 37, wherein machining a surgical tool having a longitudinal axis oriented at an angle with respect to a grain direction of the flat metal stock comprises machining a surgical tool having a longitudinal axis oriented orthogonal to the grain direction of the flat metal stock.

Example 39

The method of one or more of Example 36 through Example 38, wherein optimizing an operational characteristic of the surgical tool comprises: maximizing a length of the end effector; minimizing the length of the end effector; or reducing a stress in at least a portion of the surgical tool.

Example 40

The method of one or more of Example 35 through Example 39, further comprising subjecting the surgical tool to one or more metalworking processes.

Example 41

The method of Example 40, wherein subjecting the surgical tool to one or more metalworking processes comprises applying a metalworking process to a portion of the surgical tool proximal to the anti-node location in the surgical tool.

Example 42

The method of one or more of Example 40 through Example 41, wherein subjecting the surgical tool to one or more metalworking processes comprises removing a portion of mass of the surgical tool in a region bounded by a first anti-node location in the surgical tool and a second anti-node location in the surgical tool.

Example 43

The method of one or more of Example 40 through Example 42, wherein subjecting the surgical tool to one or more metalworking processes comprises subjecting the surgical tool to machining, skiving, coining, forming, forging, milling, end milling, chamfering, tumbling, sand blasting, bead blasting, or electropolishing, or any combination or combinations thereof.

Example 44

The method of one or more of Example 40 through Example 43, wherein subjecting the surgical tool to one or more metalworking processes comprises removing a portion of mass of the surgical tool in a section of the waveguide and bending the surgical tool in the section of the waveguide.

Example 45

The method of one or more of Example 40 through Example 44, wherein subjecting the surgical tool to one or more metalworking processes comprises machining a plurality of female screw threads into the proximal end of the surgical tool, wherein the female screw threads are oriented along a longitudinal axis thereof.

Example 46

The method of Example 45, wherein machining a plurality of female screw threads into the proximal end of the surgical tool comprises machining a plurality of female screw threads configured to receive a component having mating male threads that have a major dimension less than or equal to a thickness of the surgical tool, wherein the thickness comprises a distance between the first face of the surgical tool and the second face of the surgical tool.

Example 47

The method of one or more of Example 45 through Example 46, wherein machining a plurality of female screw threads into the proximal end of the surgical tool comprises machining a plurality of female screw threads configured to receive a component having mating male threads that have a major dimension greater than a thickness of the surgical tool, wherein the thickness comprises a distance between the first face of the surgical tool and the second face of the surgical tool.

Example 48

The method of one or more of Example 35 through Example 47, wherein machining a surgical tool from a portion of a flat metal stock comprises laser machining, laser machining with a tilt degree of freedom, electrical discharge machining, milling, stamping, or fine blanking.

Example 49

The method of one or more of Example 35 through Example 48, wherein machining a surgical tool from a portion of a flat metal stock comprises machining a surgical tool further comprising a first flange and a second flange, wherein the first flange extends from a first side of the surgical tool and the second flange extends from an opposing side of the surgical tool.

Example 50

The method of Example 49, wherein machining a surgical tool from a portion of a flat metal stock comprises machining a surgical tool further comprising a first flange and a second flange wherein each of the first flange and the second flange is symmetrically disposed about the node location in the surgical device.

Example 51

The method of one or more of Example 35 through Example 50, wherein machining a surgical tool from a portion of a flat metal stock comprises machining a surgical tool from a flat metal stock comprising aluminum or titanium.

Example 52

The method of one or more of Example 35 through Example 51, wherein contacting a face of a first transducer with the first face of the surgical tool comprises fixing the face of the first transducer to the first face of the surgical tool with an electrically conductive adhesive at a node location and wherein the face of the first transducer is fixed to the first face of the surgical tool with a high strength adhesive at a location away from the node location.

Example 53

The method of Example 52, wherein contacting a face of a second transducer with an opposing face of the surgical tool and opposite the first transducer comprises fixing a face of a second transducer to an opposing face of the surgical tool and opposite the first transducer with a conductive adhesive at the node location in the surgical tool and with a high strength adhesive at a location away from the node location in the surgical tool.

Example 54

An ultrasonic surgical device comprising: a surgical tool comprising a proximal transducer mounting portion defining a surface, a distal end effector end, and a waveguide disposed therebetween, the waveguide extending along a longitudinal axis; and a transducer in mechanical communication with the surface of the transducer mounting portion; wherein the transducer is configured to operate in a D31 mode with respect to the longitudinal axis of the waveguide; and wherein, upon activation by an electrical signal having a predetermined frequency component, the transducer is configured to induce a standing wave in the surgical tool to cause the end effector to vibrate, the standing wave having a wavelength proportional to the predetermined frequency component of the electrical signal.

Example 55

The ultrasonic surgical device of Example 54, wherein the surgical tool defines a lumen extending along the longitudinal axis.

Example 56

The ultrasonic surgical device of Example 54 or Example 55, wherein the proximal transducer mounting portion comprises a cylindrical prism.

Example 57

The ultrasonic surgical device of Example 56, wherein the waveguide has a circular cross-section Example 58

The ultrasonic surgical device of one or more of Example 56 through Example 57, wherein the waveguide has a rectangular cross-section.

Example 59

The ultrasonic surgical device of one or more of Example 56 through Example 58, wherein the transducer defines a hollow cylindrical portion in mechanical communication with the proximal transducer mounting portion.

Example 60

The ultrasonic surgical device of one or more of Example 56 through Example 59, wherein the transducer comprises a plurality of partial cylindrical plates and wherein each of the plurality of partial cylindrical plates is in mechanical communication with the proximal transducer mounting portion.

Example 61

The ultrasonic surgical device of Example 60, wherein each of the plurality of partial cylindrical plates is independently actuatable.

Example 62

The ultrasonic surgical device of one or more of Example 54 through Example 61, wherein the proximal transducer mounting portion comprises a prism having a plurality of flat surfaces.

Example 63

The ultrasonic surgical device of one or more of Example 56 through Example 62, wherein the transducer mounting portion further comprises a flat surface in the cylindrical prism.

Example 64

The ultrasonic surgical device of Example 63, wherein the transducer is in mechanical communication with the flat surface.

Example 65

The ultrasonic surgical device of one or more of Example 62 through Example 64, wherein the waveguide has a circular cross-section Example 66

The ultrasonic surgical device of one or more of Example 62 through Example 65, wherein the waveguide has a rectangular cross-section.

Example 67

The ultrasonic surgical device of one or more of Example 62 through Example 66, wherein the transducer comprises a plurality of plates wherein each of the plurality of plates is in mechanical communication with one of the plurality of side surfaces.

Example 68

The ultrasonic surgical device of one or more of Example 65 through Example 67, wherein each of the plurality of plates is independently actuatable by an electrical signal having a predetermined frequency component.

Example 69

The ultrasonic surgical device of one or more of Example 62 through Example 68, wherein the prism is a quadrilateral prism.

Example 70

The ultrasonic surgical device of one or more of Example 62 through Example 69, wherein the prism is a triangular prism.

Example 71

The ultrasonic surgical device of Example 70, wherein the prism is a hollow triangular prism having a plurality of inner side surfaces.

Example 72

The ultrasonic surgical device of Example 71, wherein the transducer comprises a plurality of rectangular plates wherein each of the plurality of rectangular plates is in mechanical communication with one of the plurality of inner side surfaces.

The invention claimed is:

1. An ultrasonic surgical device comprising:
a surgical tool comprising a proximal transducer mounting portion defining a surface, a distal end effector end, and a waveguide disposed therebetween, the waveguide extending along a longitudinal axis; and
a transducer in mechanical communication with the surface of the proximal transducer mounting portion;
wherein the transducer is configured to operate in a D31 mode with respect to the longitudinal axis of the waveguide, wherein in the D31 mode, an activating electric field is oriented orthogonal to the longitudinal axis of the waveguide;
wherein, upon activation by an electrical signal having a predetermined frequency component, the transducer is configured to induce a standing wave in the surgical tool to cause the end effector to vibrate, wherein the standing wave has a wavelength proportional to the predetermined frequency component of the electrical signal, and wherein the standing wave comprises a node at a node location in the surgical tool and an antinode at an antinode location in the surgical tool; and
wherein the surgical tool defines nodes and antinodes corresponding to nodes and antinodes of the induced standing wave, wherein the nodes correspond to locations of minimal displacement and the antinodes correspond to locations of maximum displacement, and wherein the proximal transducer mounting portion couples the surgical tool to a housing at the locations of minimal displacement by the standing wave.

2. The ultrasonic surgical device of claim 1, wherein the surgical tool defines a lumen extending along the longitudinal axis.

3. The ultrasonic surgical device of claim 1, wherein the proximal transducer mounting portion comprises a cylindrical prism.

4. The ultrasonic surgical device of claim 3, wherein the transducer defines a hollow cylindrical portion in mechanical communication with the proximal transducer mounting portion.

5. The ultrasonic surgical device of claim 3, wherein the transducer comprises a plurality of partial cylindrical plates and wherein each of the plurality of partial cylindrical plates is in mechanical communication with the proximal transducer mounting portion.

6. The ultrasonic surgical device of claim 3, wherein the transducer mounting portion further comprises a flat surface in the cylindrical prism and wherein the transducer is in mechanical communication with the flat surface.

7. The ultrasonic surgical device of claim 1, wherein the proximal transducer mounting portion comprises a prism having a plurality of flat surfaces.

8. The ultrasonic surgical device of claim 7, wherein the transducer comprises a plurality of plates;
wherein each of the plurality of plates is in mechanical communication with one of the plurality of flat surfaces; and
wherein each of the plurality of plates is independently actuatable by an electrical signal having a predetermined frequency component.

* * * * *